United States Patent
Cantu et al.

(10) Patent No.: US 10,117,617 B2
(45) Date of Patent: Nov. 6, 2018

(54) AUTOMATED SYSTEMS AND METHODS FOR SKIN ASSESSMENT AND EARLY DETECTION OF A LATENT PATHOGENIC BIO-SIGNAL ANOMALY

(71) Applicant: Revealix, Inc., Austin, TX (US)

(72) Inventors: Adrianna Cantu, Austin, TX (US); Gary Johnson, Mt. Madonna, CA (US)

(73) Assignee: Revealix, Inc., Austin, TX (US)

( * ) Notice: Subject to any disclaimer, the term of this patent is extended or adjusted under 35 U.S.C. 154(b) by 10 days.

(21) Appl. No.: 14/876,818

(22) Filed: Oct. 7, 2015

(65) Prior Publication Data
US 2016/0100790 A1   Apr. 14, 2016

Related U.S. Application Data

(60) Provisional application No. 62/061,536, filed on Oct. 8, 2014.

(51) Int. Cl.
*A61B 5/00* (2006.01)
*A61B 5/01* (2006.01)
*A61B 5/053* (2006.01)
*A61B 5/107* (2006.01)
*A61B 5/145* (2006.01)

(52) U.S. Cl.
CPC .......... *A61B 5/445* (2013.01); *A61B 5/0064* (2013.01); *A61B 5/015* (2013.01); *A61B 5/72* (2013.01); *A61B 5/0002* (2013.01); *A61B 5/0531* (2013.01); *A61B 5/1075* (2013.01); *A61B 5/145* (2013.01)

(58) Field of Classification Search
USPC ........................................ 600/306
See application file for complete search history.

(56) References Cited

U.S. PATENT DOCUMENTS

| | | |
|---|---|---|
| 5,016,173 A | 5/1991 | Kenet |
| 5,588,440 A | 12/1996 | Cowie |
| 5,701,902 A | 12/1997 | Vari |
| 6,081,612 A | 6/2000 | Gutkowicz-krusin et al. |
| 6,251,070 B1 | 6/2001 | Khazaka |
| 6,381,488 B1 | 4/2002 | Dickey |

(Continued)

OTHER PUBLICATIONS

International Search Report for PCT Application No. PCT/US15/54431 dated Jan. 8, 2016, 8 pages.

(Continued)

*Primary Examiner* — Etsub Berhanu
(74) *Attorney, Agent, or Firm* — Amin, Turocy & Watson, LLP

(57) ABSTRACT

The present invention relates to systems and methods for early detection, assessment, monitoring and prevention of pathophysiological conditions originating and/or emanating from skin or localized tissues, including but not limited to acute or chronic episodes of soft tissue pathology, wound, injury, dermatological or rheumatoid condition where bio-signal patterns, biomarkers or other identifiable elements or references would deviate from baseline. Specifically, the present invention relates to methods and systems specially designed and adapted for early detection of a latent pathogenic bio-signal anomaly using multiple aggregated sensors before the anomaly would otherwise be detectable.

16 Claims, 22 Drawing Sheets

(56) References Cited

U.S. PATENT DOCUMENTS

| | | |
|---|---|---|
| 6,533,725 B1 | 3/2003 | Endo |
| 6,648,820 B1 | 11/2003 | Sarel |
| 6,944,491 B2 | 9/2005 | Leveque |
| 7,233,693 B2 | 6/2007 | Momma |
| 7,359,748 B1 | 4/2008 | Drugge |
| 7,428,468 B2 | 9/2008 | Takemura |
| 7,546,156 B2 | 6/2009 | Madden |
| 7,657,125 B2 | 2/2010 | Allen |
| 7,894,651 B2 | 2/2011 | Gutkowicz-krusin |
| 8,019,624 B2 | 9/2011 | Malone |
| 8,026,942 B2 | 9/2011 | Payonk |
| 8,062,220 B2 | 11/2011 | Kurtz |
| 8,496,695 B2 | 7/2013 | Kang |
| 8,532,736 B1 | 9/2013 | Malzbender |
| 8,761,476 B2 | 6/2014 | Burlina |
| 8,923,954 B2 | 12/2014 | Herman |
| 8,953,837 B2 | 2/2015 | Gilad-gilor |
| 2003/0012457 A1* | 1/2003 | Solecki ............... G06T 3/4023 382/299 |
| 2003/0213892 A1* | 11/2003 | Zhao ................. H01L 27/146 250/208.1 |
| 2007/0003155 A1* | 1/2007 | Miller ............ G06K 9/0063 382/254 |
| 2008/0161661 A1* | 7/2008 | Gizewski ........... A61B 5/0059 600/306 |
| 2010/0185064 A1 | 7/2010 | Bandic et al. |
| 2013/0109977 A1 | 5/2013 | Nikzad |
| 2013/0172696 A1 | 7/2013 | Riesinger |
| 2013/0208102 A1 | 8/2013 | Kim |
| 2013/0253335 A1 | 9/2013 | Noto |
| 2013/0310696 A1 | 11/2013 | Ribble |
| 2014/0155755 A1 | 6/2014 | Pinter et al. |
| 2014/0155763 A1 | 6/2014 | Bruce |
| 2014/0194722 A1 | 7/2014 | Lee |
| 2014/0213936 A1 | 7/2014 | Monovoukas |
| 2014/0221847 A1 | 8/2014 | Dubielczyk |
| 2014/0316235 A1* | 10/2014 | Davis ............. A61B 5/7246 600/407 |
| 2014/0357990 A1 | 12/2014 | Wang |
| 2015/0025343 A1 | 1/2015 | Gareau |
| 2015/0025412 A1 | 1/2015 | Gillman |
| 2015/0119721 A1 | 4/2015 | Pedersen |
| 2015/0216422 A1 | 8/2015 | Beilin |
| 2015/0223695 A1 | 8/2015 | Chong |
| 2015/0247999 A1 | 9/2015 | Ntziachristos |

OTHER PUBLICATIONS

Szentkuti, A; et al: Infrared thermography and image analysis for biomedical use, Periodicum Biologorum. Sep. 2, 2011. vol. 113, No. 4; pp. 385-392.

* cited by examiner

Computation of SKEWS Score 1800

Sub-score values 1810 (0 – 5)

No Risk 0
Min Risk 1
Mod Risk 2
High Risk 3
Severe Risk 4
Active Injury 5

SKEWS values 1811 (0 – 35)

No Risk 0 -6
Min Risk 7-12
Mod Risk 13-20
High Risk 21-26
Severe Risk > 26

| Score Categories | No Risk 0 | Min Risk 1 | Mod Risk 2 | High Risk 3 | Severe Risk 4 | Active Injury 5 |
|---|---|---|---|---|---|---|
| 1801 Risk Profile for Injury/Wound Development | | | 2 | | | |
| 1802 Bio-signal Profile | | | 2 | | | |
| 1803 Wound/Injury/Condition | | | | | | 5 |
| 1804 Peri-wound,-injury,-condition Status | | 1 | | | | |
| 1805 Wound Bed Status | | 1 | | | | |
| 1806 Wound Edge/Margin | | | | | | |
| 1807 Vascular Status | | | | 3 | | |
| *SKEWS Sub-scores 1808* | 0 | 2 | 4 | 3 | 4 | 5 |
| SKEWS 1809 | 18 | | | | | |

Figure 18

AUTOMATED SYSTEMS AND METHODS FOR SKIN ASSESSMENT AND EARLY DETECTION OF A LATENT PATHOGENIC BIO-SIGNAL ANOMALY

CROSS-REFERENCE TO RELATED APPLICATIONS

This application claims the benefit of U.S. Provisional Patent Application No. 62/061,536, filed Oct. 8, 2014, the disclosure of which is hereby incorporated herein by reference in its entirety.

BACKGROUND OF THE INVENTION

Preventable injuries are frequent and pervasive amongst the most vulnerable and fastest growing patient populations worldwide, the elderly and diabetic. In particular, healthcare providers struggle to mitigate preventable injuries in the body's largest organ, the skin and associated soft tissue. They simply lack the tools to identify the earliest signs of emerging skin and wound complications, thus missing the most critical time to intervene and reduce injury incidence and/or severity. These preventable skin injuries account for nearly $40 billion of costs to the healthcare industry in the U.S. alone.

In the U.S. alone over 40 million patients per year will be cared for throughout more than 5,000 hospitals, 15,000 nursing homes and 12,000 home health agencies. The majority of these admissions represent "at-risk" patient populations. For diabetics, an mHealth solution like this one provides early detection capabilities via self-monitoring.

In October 2014 Medicare penalties for preventable skin injuries came into particular focus. Two key programs, Hospital Acquired Condition and Hospital Readmissions Reduction Program, impose dramatic financial repercussions onto hospitals with poor rates of performance. With payment denials and unprecedented penalties of up to 3% across all Medicare dollars, the financial stakes related to skin and wound management outcomes have never been higher. Prevention is critical.

Monitoring skin integrity, skin based clinical parameters and wound status is an integral component to the prevention and management of wounds and/or underlying physiological conditions. Treatment and/or intervention decisions are based on clinical impressions and observations, but conventional methods of skin integrity and/or soft tissue assessment rely heavily on subjective detection and interpretation of subtle clinical cues. This subjectivity in manual and/or other heuristic clinical assessment techniques introduces variability into care pathways from the moment of initial assessment and through to subsequent inspections. Advances in sensor technologies coupled with mobile capabilities and the digitalization of clinical documentation allow for development of more objective, practical and economical tools for use at the point of care. Development of a valid and reliable tool to objectively capture relevant parameters of skin and/or condition assessment leverages technology to introduce an innovative approach to improve patient safety, quality and coordination of care.

Technology advancements are occurring but tend to focus on monitoring compliance with a particular process of care. Next generation solutions, such as disclosed herein, allow early detection and strategically incorporate a wide range of clinically and operationally meaningful throughput capabilities focused on data sciences and full stack integration.

SUMMARY OF THE INVENTION

The present disclosure relates to early detection, assessment, monitoring and prevention of pathophysiological conditions originating and/or emanating from skin or localized tissues, including but not limited to acute or chronic episodes of soft tissue pathology, wound, injury, dermatological or rheumatoid condition where bio-signal patterns, biomarkers or other identifiable elements or references would deviate from baseline.

BRIEF DESCRIPTION OF THE DRAWINGS

The accompanying drawing figures incorporated in and forming a part of this specification illustrate several aspects of the invention, and together with the description serve to explain the principles of the invention. The above and other objects and advantages of the present invention will be apparent upon consideration of the following detailed description, taken in conjunction with the accompanying drawings, in which like reference characters refer to like parts throughout, and in which:

FIG. 18 illustrates an embodiment of a computer-generated pathophysiological condition scoring mechanism (including but not limited to assessing relevant pathogenic bio-signal anomaly such as a wound, injury, dermatogenic or rheumatoid condition bio-signals) that combines elements of a set of specific mappings to generate a tissue status or skin and/or wound score.

DETAILED DESCRIPTION OF THE INVENTION

The embodiments set forth below represent the necessary information to enable those skilled in the art to practice the invention and illustrate the best mode of practicing the invention. Upon reading the following description in light of the accompanying drawing figures, those skilled in the art will understand the concepts of the invention and will recognize applications of these concepts not particularly addressed herein. It should be understood that these concepts and applications fall within the scope of the disclosure and the accompanying claims.

Figure 1:
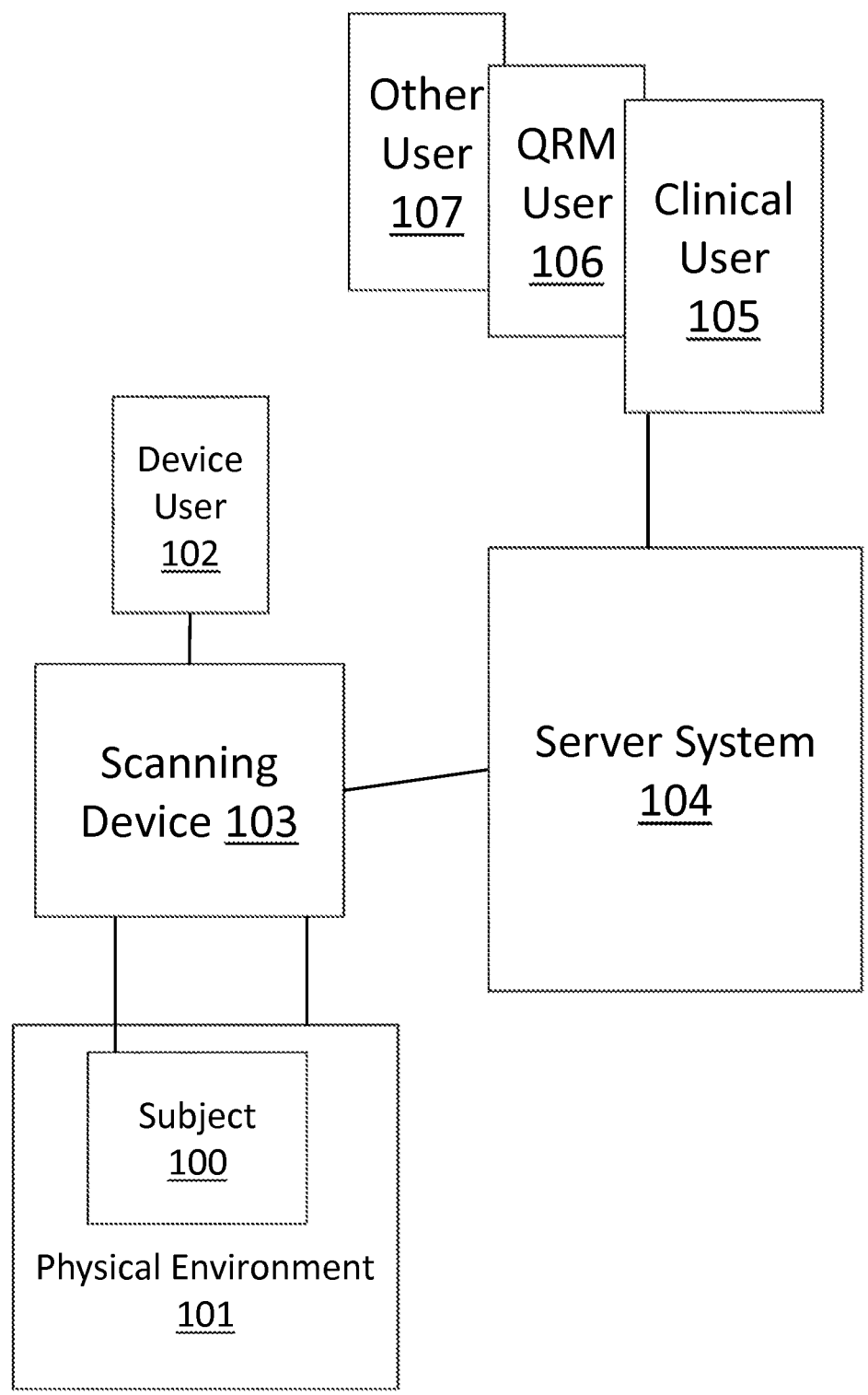
FIG. 1 illustrates the high-level context of this disclosure, including how a scanning device and associated server system interact with the subject, their physical environment, and other users of the system.

FIG. 1 illustrates a system that includes a scanning device 103 and a server system 104 that are used to acquire sensor data from the subject 100, where the subject can be but is not limited to a hospital patient, clinic patient, home-care patient; in general a person who is either having their health monitored or is self-monitoring their own health. The scanning device is used by the device user 102, where the device user can be but is not limited to a nurse, doctor, home-health care worker, caregiver (including family members and friends), health practitioner, health professional, health technician or any other $3^{rd}$ party authorized (i.e. retail clinic personnel) to operate the device with or without human intervention, or in the case of subject self-care, the subject themselves. The scanning device is designed to acquire relevant bio-signals from the subject, which may include but are not limited to chemical signals, ultrasound signals, visual, infrared and hyper-spectral light signals, and impedance signals, which individually or in combination can be used to enable early detection of the latent pathogenic bio-signal anomalies of a wound or other skin condition. As used herein, wounds or other skin conditions include pathophysiological conditions that manifest in the skin or soft tissues such as inflammatory conditions that manifest in skin or soft tissues including dermatological conditions.

To fully acquire the bio-signals the scanning device can incorporate 3 or more modes of operation passive, active or a hybrid combination of both depending on mode and timing of operation. In a passive mode it is in a receive-only mode measuring and detecting various bio-signals. Whereas in an active mode the scanning device (either alone or with other external devices) induces, transmits various stimulate into the body or environment and then monitors and measures the response. A hybrid mode is a combination of both types either simultaneously or time-sliced. The scanning device is also designed to acquire relevant signals from the subject's environment, which may include but are not limited to environmental signals such as ambient light, temperature and humidity, but also situational signals such as positioning, and location, as well as signals that may help aid the processing of the bio- and environmental signals such as depth-of-view, and other such signals.

The signals that are captured by the scanning device can be processed locally on the device, and can be sent to the server system 104 for further processing. In one embodiment, the signals are processed completely on the scanning device. In another embodiment, the signals are not processed on the device but are sent to the server system for processing. In yet another embodiment, the signals are processed on both the scanning device and in the server system, based on a calculation of where best the processing can be accomplished using criteria such as processing complexity, response time, processing capabilities, value to the subject or device user, or value to other users in the system 105, 106, 107, or other criteria.

The server system 104 is designed to receive information from the scanning device, for the purpose of, but not limited to, storage and retrieval, analysis, prediction, trending, alerting, and integration with existing health care or other systems. The information received from the scanning device includes but is not limited to bio-signals and environmental signals from the subject and their physical environment, abstractions, representations, extrapolations or derivations or other secondary processing of the original signals, or information derived from these primary signals such as alerts or messages relating to the signals, and can also include non-alterable time-stamp and geo-location information. In one embodiment the information is encrypted and secured by transmission over secure networking protocols such as HTTPS. In another embodiment the information is encrypted in a manner that allows third-party access to the information (for example for escrow purposes). The server system is designed to transmit information to the scanning device, including abstractions, representations, extrapolations or derivations or other secondary processing of the original signals, or information derived from these primary signals such as alerts or messages relating to the signals. In one embodiment the information is encrypted and secured by transmission over secure networking protocols such as HTTPS. In another embodiment the information is encrypted in a manner that allows third-party access to the information (for example for escrow purposes).

The server system is also designed to allow access to the transmitted and received information by other users, including clinical users 105, quality and risk management (QRM) users 106, and other users 107. The server system is designed to provide information to these users that allows them to process, interpret, and otherwise act upon information that they receive from the system. In one embodiment, the server system comprises a web application that allows said user to access the information using a web browser (such as Google Chrome). In another embodiment, the server system comprises a set of "plug-ins" to existing health record systems (electronic health records or electronic medical records), allowing information from this system to be displayed and/or otherwise acted upon using existing, deployed software systems. In yet another embodiment, both access methods are deployed based on the requirements of individual users of the system. In yet another embodiment, access to the information is retrieved directly from another server that provides access, processing or storage of the information without human intervention.

Figure 2:
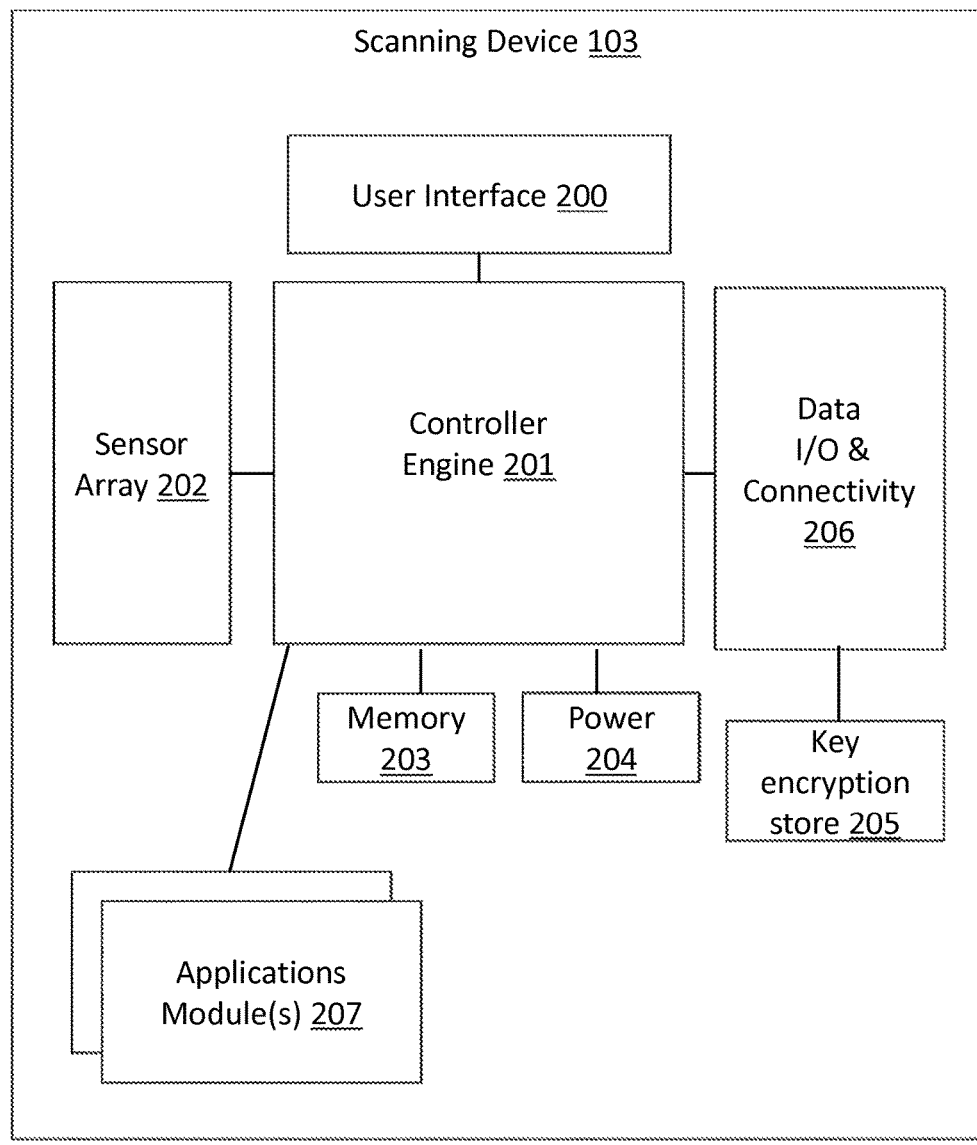
FIG. 2 illustrates the system-level details of the scanning device, including a central controller engine, user interface, sensor array, data input/output module and other important functional and/or logical blocks.

FIG. 2 illustrates a scanning device 103 that provides sensor data input from a subject 100 and their physical environment 101. In one embodiment, the scanning device is comprised of a smartphone platform with sensors integrated via associated accessory interfaces (such as an iPhone with MFi accessory protocol), or via other accessory integration methods such as Wi-Fi, Bluetooth, Bluetooth Low Energy (BLE), or other integration technologies. In another embodiment, the scanning device is a custom hand-held hardware device, which allows non-contact and/or with-contact sensor data acquisition. In another embodiment, the scanning device may be mounted on a wall, ceiling, workstation or bed. In another embodiment, the scanning device is a wearable device, similar to Google Glass, which is worn by the device user 102 on the head, face, wrist or other location on the body. In all embodiments the scanning device is designed to collect relevant sensor data from the subject and their physical environment to be processed by the system as a whole, by taking Sensor input from the Sensor Array 202, processing it within the controller engine 201, which uses associated system Memory 203 and Power 204 modules to perform processing operations on the input, and either sending results directly to the user interface 200, or to the Data I/O Connectivity module 206 for transmission to the rest of the system, or in some embodiments, a combination of the two operations. FIG. 2 furthermore shows the application module(s) 207 component of the scanning device. Application modules create and deploy device-based applications, which incorporate business logic, user interface, network connectivity and data storage by leveraging the components of the Scanning system that provide these services 200-206, along with providing application-specific services themselves. In the preferred embodiment, an instance of an application module would be implemented as a stand-alone software program that allows interaction with said scanning device components, implemented in terms of application programming interface (API) technology, whereby application-specific functionality is available on the scanning device via access to these APIs. As shown in FIG. 2, one or many application modules can be running independently and in parallel in the preferred embodiment.

Figure 3:
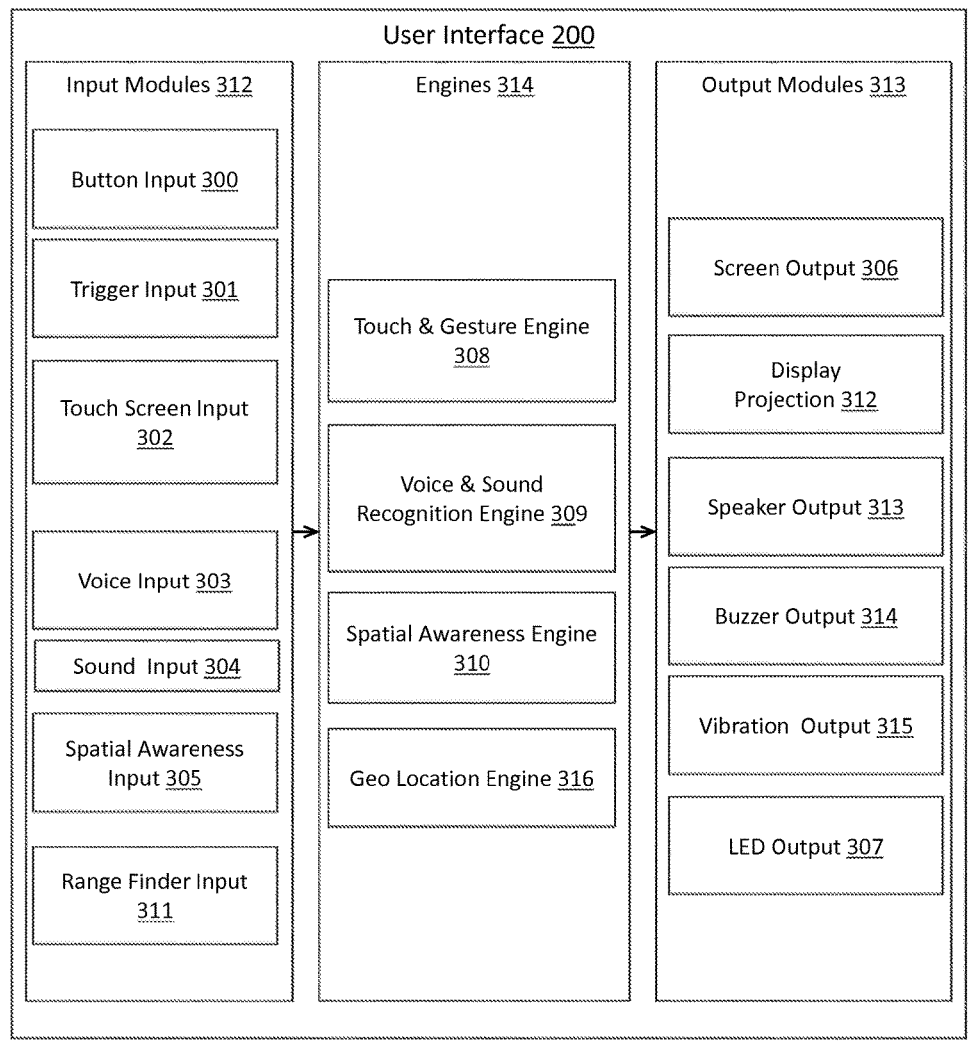
FIG. 3 illustrates in more detail the user interface component of the scanning device, including various methods of retrieving input from the device user and providing output to the device user, as well as the internal engines used to process said input/output.

FIG. 3 illustrates the user interface 200 internal module of the scanning device. The user interface module is generally comprised of input modules 312 that are responsible for collecting input from various hardware input devices, such as, but not limited to, buttons 300, triggers 301, touch screens 302, microphones (for both voice 303 and other sound input 304) accelerometers 305, gyros 305, range finders 311 and cameras. Engines 314 are modules that process inputs from the input modules and in some embodiments render them into higher-level forms that can be interpreted more readily by the system. In an embodiment, a touch and gesture engine 308 may render physical touches on a touch screen, retrieved by the touch screen input module 302, and render that input into a gesture such as a "swipe", which could be interpreted by the system to mean a specific command. Similarly, the voice and sound recognition engine 309 may process input from the voice input or sound input module and render that input into specific commands that are interpreted by the system. In a similar manner, the spatial awareness engine 310 and geo location engine 316 will process input from the spatial awareness input 305 and range finder input 311 modules to provide information to the system on where the scanning device is located in absolute space or relative to the subject or their physical environment. The higher-order output of the engine modules can be sent to the output modules to provide feedback or information to the device user.

In other embodiments the input from the input modules may be left unprocessed and passed to the output modules 313, which are responsible for sending feedback or information to the device user. In either form of embodiment, output modules can include but are not limited to screen output 306, display projection 312, which can project, using pico-projector or similar technology, information on the subject's body or clothing, or on the subject's physical environment such as but not limited to the subject's hospital bed, or other aspects of the subject's environment. Output modules can include speaker output 313, buzzer 314 or vibration output 315, as well as simple LED output 307.

In one embodiment the user interface module works to facilitate efficient device user workflow by enabling the device user to use only one hand to operate the scanning device. In this embodiment, the scanning device recognizes a combination of voice commands from the device user, movement of the scanning device to indicate mode of operation (gesture recognition, for example by moving the scanning device in a circular motion to generate a command), and spatial orientation of the scanning device, potentially using SLAM, to determine both orientation and location of scanner over body locations. In this embodiment the user interface may also respond to a simple trigger or button to facilitate command input. The use of these mechanisms thereby allow the device user to use his/her second hand to steady the subject, also keeping the scanning device less contaminated from subject or their physical environment.

In this embodiment, the scanning device gives easy-to-understand and intuitive feedback to the device user, including the use of:

Vibration or squeak noise to indicate device status

Projected light onto patient—indicating patterns/problems

Projected light onto clipboard to allow simply data entry to select choices of patient status//then use camera/gyro to read result Additionally, the embodiment provides workflow improvement by removing user entry errors by and easing workload, by automatic location of patient bed from geo-location, scanning of subject identification by barcode recognition or similar technology, and scanning of the subject's physical environment.

Figure 14:
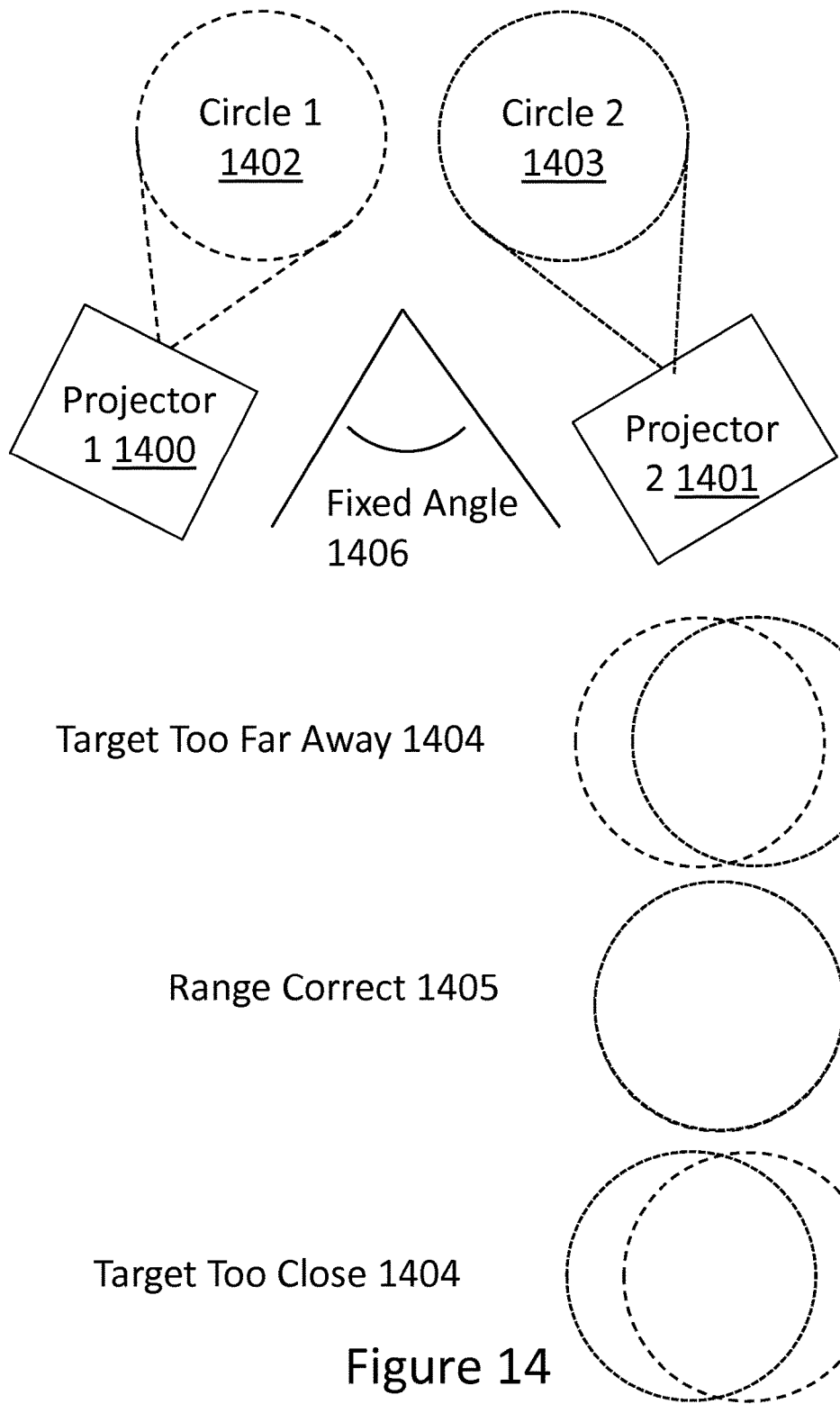
FIG. 14 illustrates an embodiment of projected user interface elements, specifically for determining correct range to target.

In an embodiment of the user interface module shown in FIG. 14, the system uses visible light projection onto the subject's skin to assist diagnosis, feedback, training, and bio-signal collection. In one embodiment, the mechanism is used to ensure correct target range. In another embodiment, a hologram-style depiction of involved areas can show device users in real-time where hotspots are, along with a visual indication of their profile (depicting injury patterns visually at the point of care vs. just on the scanning device or the server system. Colored, patterned or shaped images are projected as either images or videos (to produce movement) onto the subject's skin by projector 1 1400 and projector 2 1401, which are mounted in a fixed, angled position 1406 on the scanning device. A specific pattern is generated when the target distance is too far from the desired range 1404 (or 1408), similarly a specific pattern is generated when the target distance is too close 1404, and the projected images are aligned when the target distance is correct. Correct positioning, including range from target, could also be assisted with audio or sound feedback. Furthermore, the embodiment may have the ability to correctly place the projected image or video if the scanning device is moved or in motion moving utilizing SLAM (Simultaneous localization and mapping) to keep track of the machine's location in the physical environment.

Figure 15:
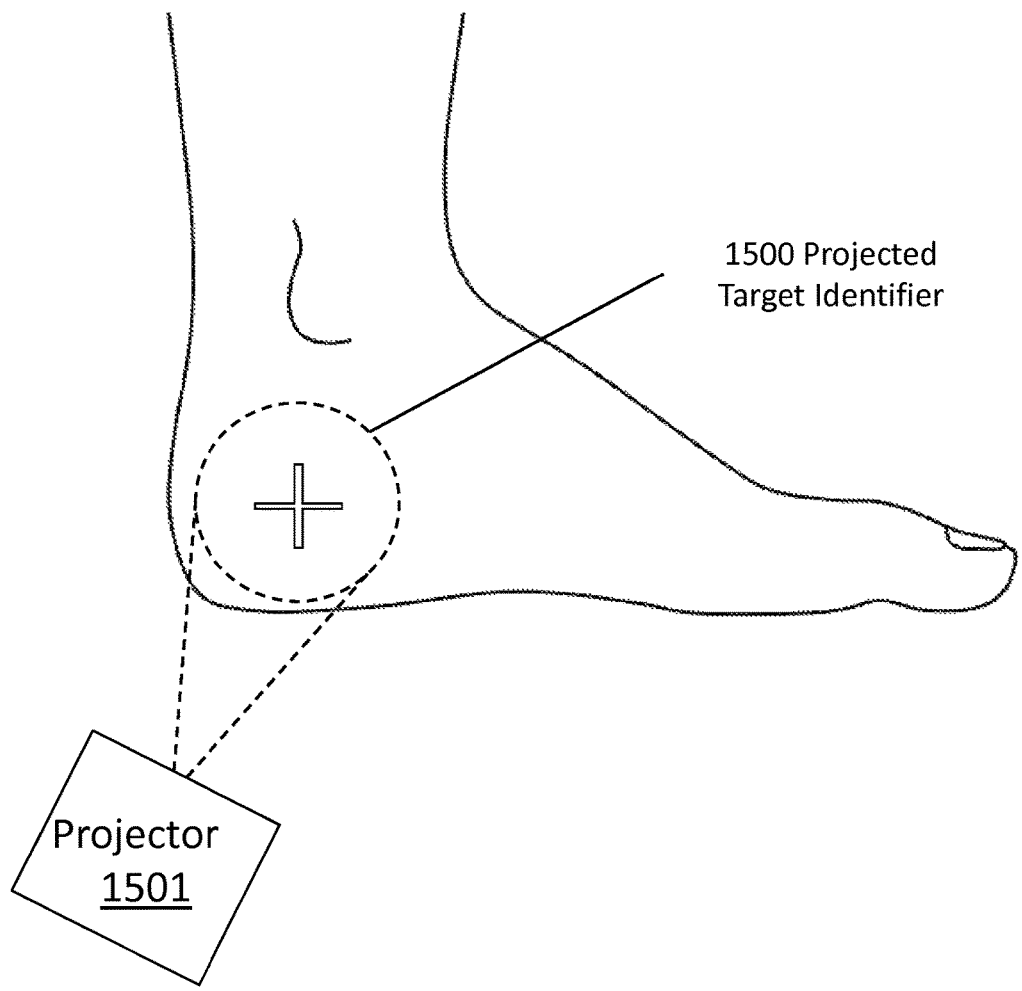
FIG. 15 illustrates an embodiment of projected user interface elements, specifically for locating correct target placement.

In another specific embodiment, FIG. 15 illustrates a mechanism for projecting a target 1500 onto the subject's skin in order to facilitate the correct location for data acquisition. As above, colored, patterned or shaped images are projected as either images or videos (to produce movement) onto the subject's skin by a Projector 1501, which is mounted on the scanning device. A specific pattern is generated when the target is in the correct location on the subject's limb, either by using specific geometry of the subject limb to change the appearance of the projected image, or by the scanning device recognizing its relative position to the subject limb and modifying the projected image accordingly.

Figure 16:
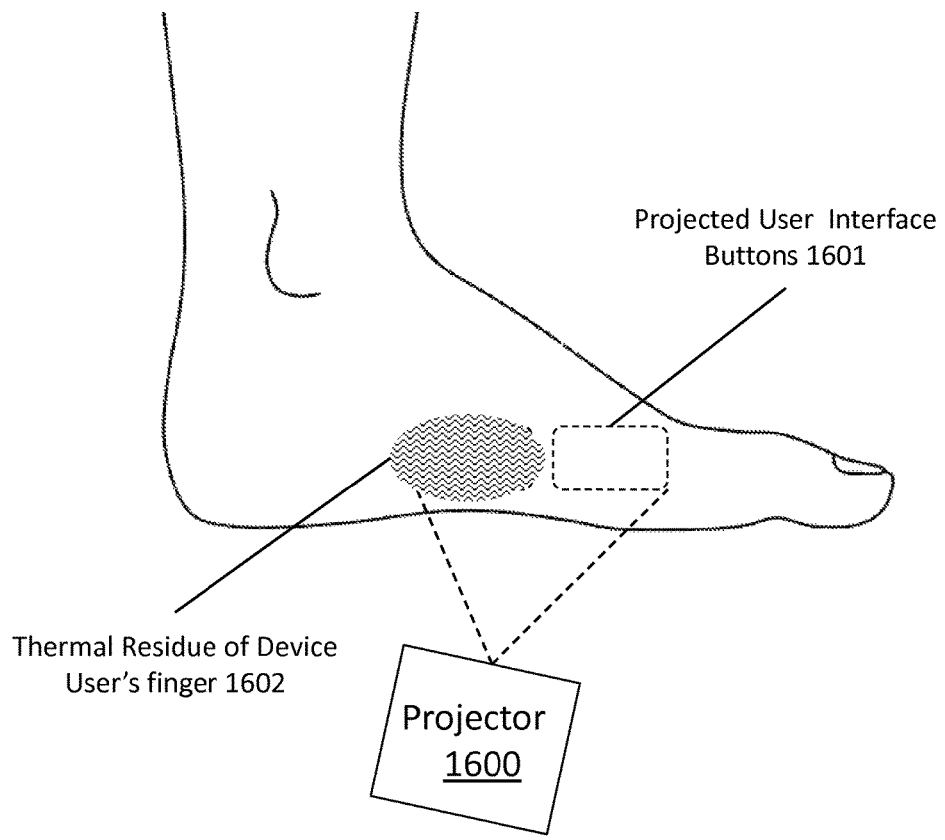
FIG. 16 illustrates an embodiment of interactive projected user interface elements, where the thermal residue of the device user's finger can be used to determine what interaction was performed.

In another embodiment, FIG. 16 illustrates visible light projection onto the subject's skin and user interface interaction by the device user's touching the skin (away from suspected damaged area). A Projector 1600 projects a set of user interface buttons 1601, and a thermal imager in the scanning device searches for thermal residue from the device user's finger. After the device user touches the skin, the scanning device uses image and/or video recognition to recognize the thermal residue "fingerprint" left on the skin UI after the finger is removed, thus recording the touch as a user interface button press.

Figure 22:
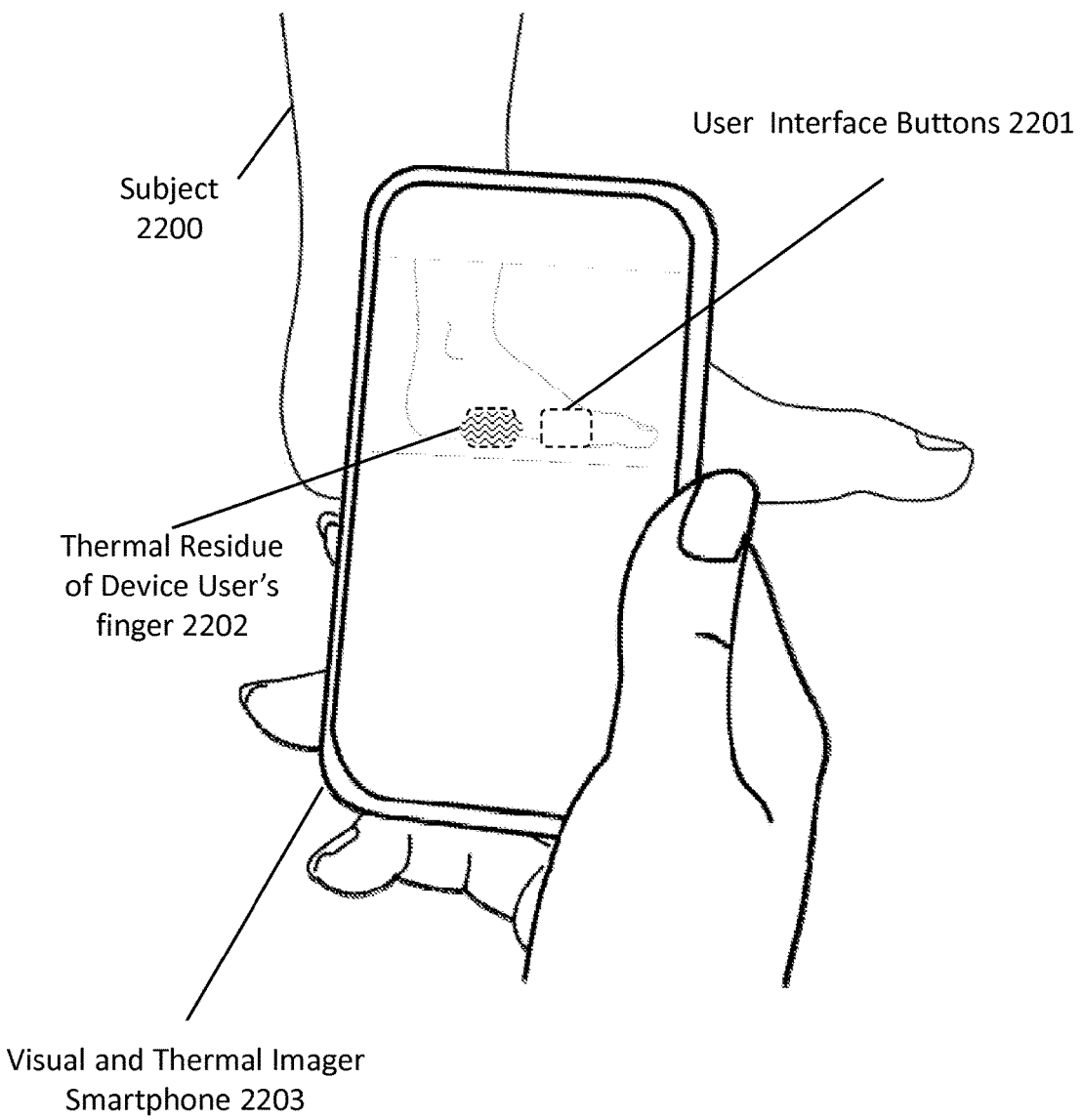
FIG. 22 shows an example user interface of the present invention.

In another embodiment, FIG. 22 illustrates user interface interaction by the device user's touching the skin (away from suspected damaged area). In this embodiment, the scanning device is based on a smartphone, such as but not limited to an iPhone or Android phone or other device that has display capability, and that has both visible and thermal imagers 2203. The visible-light camera takes a succession of real-time images of the subject area of interest and displays the area within the screen of the smartphone. Using image processing feature-matching techniques such as but not limited to edge or corner detection, or object-matching techniques such as but not limited to those based on machine learning techniques, the scanning device tracks the movement of the subject Area, while the thermal imager in the scanning device searches for thermal residue from the device user's finger. After the device user touches the skin, the scanning device uses image recognition techniques to recognize the position of the thermal residue "fingerprint" left on skin UI after the finger is removed relative to the subject Area, thus recording the touch as a user interface button press. Where the registered touch is recorded relative to the image can also allow multiple "button" types on the skin surface mimicking a series of different function buttons.

Figure 4:
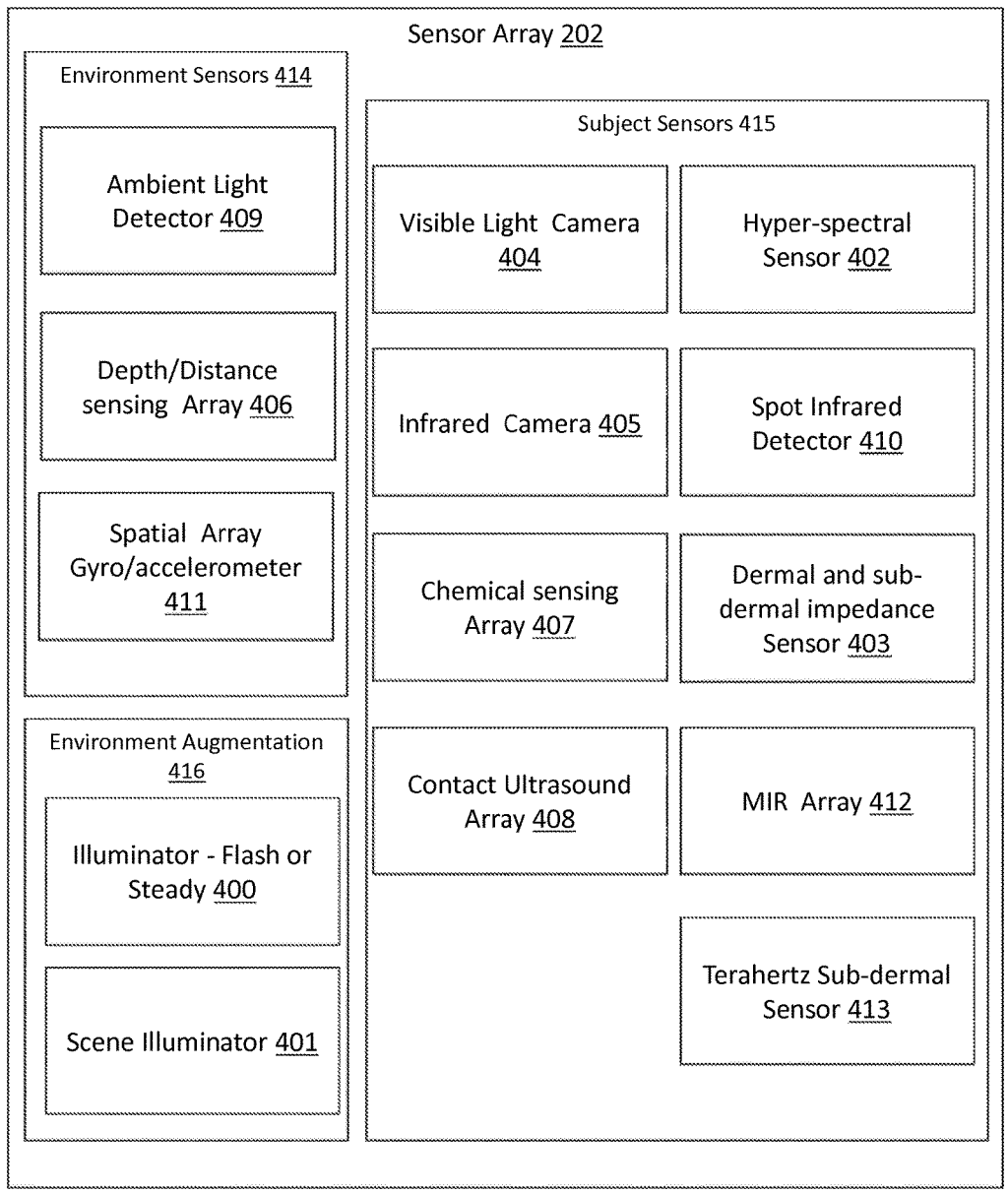
FIG. 4 illustrates in more detail the sensor array component of the scanning device, including the various sensor input types that are supported (subject and environment) and those for environment augmentation (subject illumination).

FIG. 4 illustrates in more detail the Sensor Array 202 component of the scanning device, which is comprised of environment sensors 414, subject sensors 415, and environmental augmentation sensors 416. Environment sensors are designed to collect input from the subject's physical environment, including ambient light 409, depth and distance 406, using one of but not limited to laser, sonar, structured light, SLAM (simultaneous localization and mapping), or other depth/distance detection technologies, and spatial array gyroscope or accelerometer 411. Environmental augmentation sensors include illuminators—flash or steady 400 or scene illuminators 401, which in one embodiment may include external coordination with external devices such as but not limited to room lighting or other light sources. Subject sensors are designed to collect input bio-signals from the subject, and include but are not limited to front- or back-facing visible light camera 404, infrared camera 405, chemical sensing array 407, contact ultrasound array 408, hyper-spectral sensor 402, spot infrared detector 410, dermal and sub-dermal impedance sensor 403, MIR array 412, and terahertz sub-dermal sensor 413. These sensor inputs are sent to the controller engine 201 for processing by the scanning device.

In on embodiment, a monitoring system for early detection of a latent pathogenic bio-signal anomaly in a patient includes a housing sized to be hand-held, a visual sensor in the housing, a thermal sensor in the housing, a visible-light projector in the housing to project user interface elements onto the skin of the patient, and a controller engine and memory. The controller engine and memory acquire and store data from the visual sensor and the thermal sensor, combine the visual sensor data and the thermal sensor data and compare the combination to a baseline of combined visual sensor data and thermal sensor data to determine if the latent pathogenic bio-signal anomaly is present. The visual sensor also detects user interactions with the projected user interface elements, and the thermal sensor also detects user interactions with the projected user interface elements. The visual sensor can be a camera, light sensor, or similar sensor, and the thermal sensor can be an infrared sensor or similar sensor. In other embodiments, the monitoring system may not include the visual sensor or the thermal sensor. The above example provides an efficient monitoring system because it uses the thermal sensor for both determining if the latent pathogenic bio-signal anomaly is present and for detecting user interactions with projected user interface. The use of combined visual and thermal data allows for detection of latent pathogenic bio-signal anomalies that would not otherwise be clinically significant.

In one embodiment the scanning device includes an array of sensor modules that, when placed in proximity to a subject and region of interest (ROI), is capable of detecting thermal bio-signals produced and emanating from skin or localized tissues. This capability enables capturing, imaging, analysis and monitoring of clinically meaningful temperature patterns/profiles at early onset of injury, ulceration, pathophysiological condition and/or healing complication, prior to the emergence of visual and/or tactile cues. Thermal bio-signal changes at superficial tissues can be used to evaluate underlying pathogenic processes associated with injury and/or complications. Prior studies have demonstrated that the temperature profile of certain aspects of the diabetic foot provides a reliable warning of tissue injury. Likewise, other studies targeting pressure related injury have concluded that monitoring temperature profiles among at risk patients can help clinicians relate findings to key physiological changes in order to identify early stages of injury or underlying inflammatory condition. Preclinical studies and forensic examinations suggest it takes 7 to 14 days for the effects of injured tissue to become visible. Thus the scanning device and system detects "early warning" signs, such as inflammatory-phase bio-signals, which provide early warning of the onset of injury and/or healing complication, and thermal asymmetries, variances and/or demarcations (gradient or frank), which provide early recognition of underlying tissue perfusion impairment or dysfunction, including relative tissue ischemia/hypoxia.

Other examples of situations that can be diagnosed with thermal bio-signals include, but are not limited to:
  Friction, shear and/or pressure related injury; including DTI
  Infection at soft-tissue surgical site
  Infection at entry/exit sites for venous or arterial catheters
  Infection at exit sites for surgical drainage tubes
  Infection at wounds/soft-tissues injuries
  Infection at Charcot foot
  Infection at DFU, min=<2 m inflammation, mod=>2 cm (the extent of inflammation around a diabetic foot ulcer can be measured to classify the severity of infection (mild-erythema>0.5 cm but <2 cm; mod->2 cm, severe goes beyond local issues and is systemic . . . ))
  Under-perfused skin/tissues due to ischemic toe/digit, distal extremity
  Under-perfused skin/tissues due to allograft rejection/failure
  Under-perfused skin/tissues due to post-surgical-flap failure (i.e., amp. site)

In another embodiment, the scanning device includes an array of sensor modules that provides capabilities that enable sequential, time-lapsed or dynamic detection, imaging and analysis of thermal fluctuation, asymmetry and/or demarcation patterns manifesting in a subject's skin in response to induced or underlying stimuli (thermal flux screening). Thus the scanning device and system detect thermal flux at skin and superficial tissues enables dynamic screening and/or adjunctive monitoring of certain conditions associated with altered, pathophysiological tissue perfusion or inflammatory state, including, but not limited to conditions induced or contributed to by underlying peripheral vascular/vasoactive mechanisms or inflammatory type responses induced, and manifesting in the subject's skin. The scanning device and system may allow the device user to compare between affected and unaffected subject limbs or other ROI (regions of interest). In summary, the scanning device can enable existing vascular, allergy and other clinical screening techniques to be conducted in an automated, quantifiable/objective and cost effective manner vs. existing, mostly manual approaches. Additionally, the system can provide training techniques, including video coaching, that monitors and coach the technique used by a health-worker in performing the various tests using the scanning device and system.

Other examples of situations that can be diagnosed with sequential, time-lapsed or dynamic thermal bio-signals include, but are not limited to:
  Raynaud's Disease
  Vascular Screening/LE
    Capillary Refill Time (CRT)
    PrU Blanch Test
    Venous Filling Time
    Rubor of Dependency
  Reflex sympathetic dystrophy (RSD)//complex regional pain syndrome (CRPS)

Further clinical applications that benefit from this non-invasive thermal screening, by extracting bio-signal information about blood circulation, local tissue metabolism, sweat gland malfunction, inflammation and healing, include:
  Extremity musculoskeletal/neuro-musculo-skeletal disorders
    Carpal tunnel syndrome
    Thoracic outlet syndrome
    Neurovascular disorder testing for damage resulting from Type 2 Diabetes
    Joint disorders/joint injury
  Dentistry/dental disorders
    Perfusion at gums/tooth viability
    TMJ
  Vascular/Neurovascular disorders
    Sympathetic vasomotor disorders
  Rheumatology disorders
    Raynaud's Phenomenon (RP)
    Psoriatic Conditions
    Eczema
  Bone disorders/disease (at areas where bone is close to skin surface)
    Tibia, ankle/foot, wrist/hand
    Charcot fractures (foot)
    Osteitis Deformans "chronic inflammation of bone"
  Sports/Rehab Medicine
    Dermatome patterns—Nerve impairments/impingements
  Veterinary medicine (includes others)
    Inflammatory conditions at tendons, joints
    Peripheral neurovascular disorders In one embodiment, the scanning device allows skin surveillance capabilities from a distance of up to 30 feet using various mounting options. In this embodiment, the scanning device easily affixes to a wall, bedframe or existing medical equipment (for example, the WOW—workstation on wheels) to customize the surveillance target. Using computer vision and object recognition techniques, automatic ranging and SLAM (simultaneous localization and mapping) either within the scanning device itself or within the system comprising the scanning device and the server system, the scanning device Looks for un-covered "key area" and listens, records videos and photos, enabling hands free monitoring during hands-on skin assessment, and enabling continuous or time lapsed monitoring. Using the aforementioned techniques, the system can perform patient limb recognition and can detect and account for deformities, swelling, and amputations.

Figure 11:
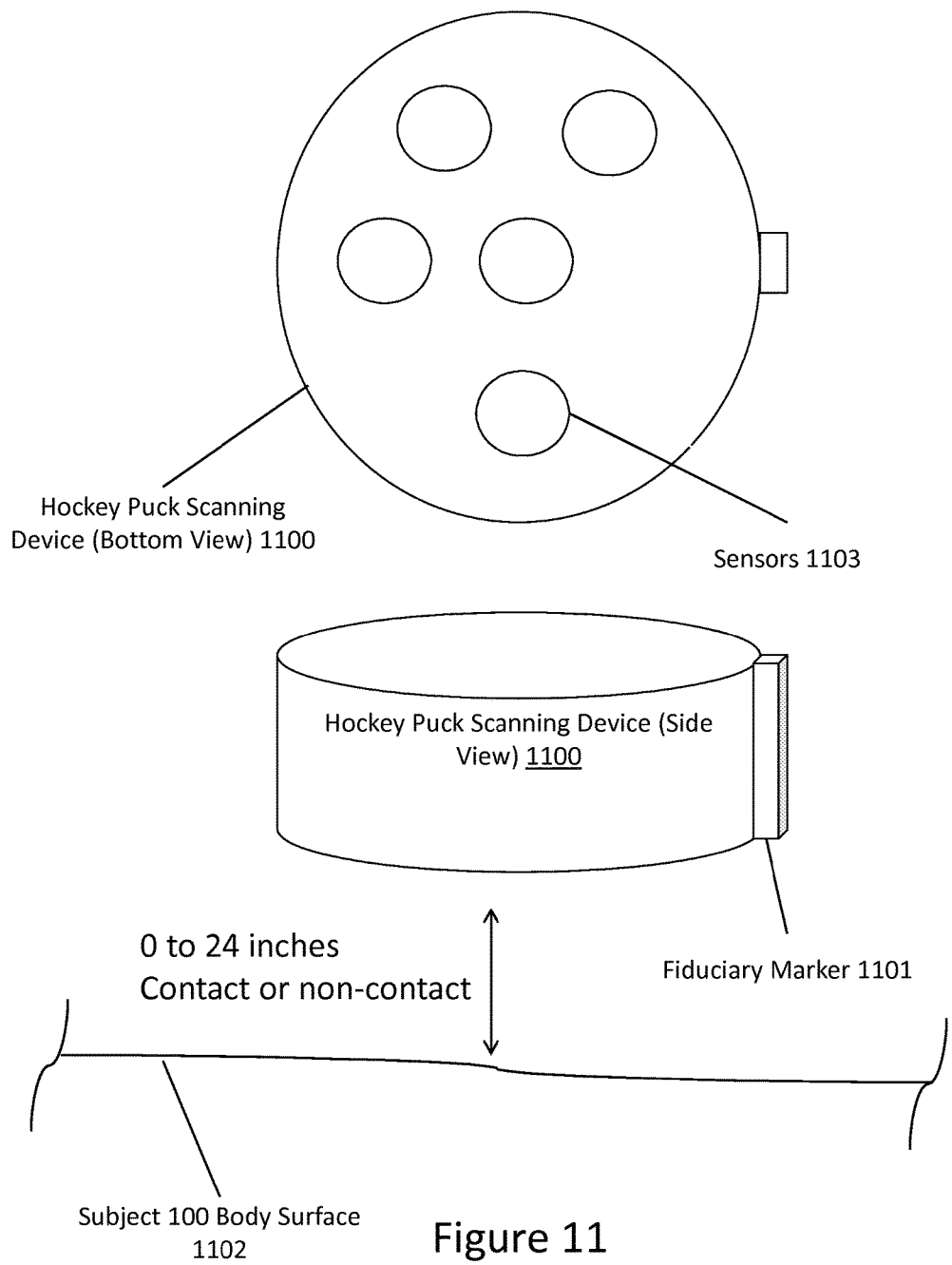
FIG. 11 illustrates one embodiment of a hand-held scanning device showing its intended usage, physical configuration and sensors.

In an example of the custom hand-held hardware device embodiment, FIG. 11 shows the scanning device as a palm-sized "hockey-puck" shaped device 1100, designed to be low-cost and unobtrusive in its use while interacting with the subject. In this embodiment, the device specifically does not look like a camera, to allow the subject to retain dignity and privacy, as it does not appear to be actively acquiring data on the subject. The scanning device has an ergonomic design to fit the palm of the hand easily for the device user, with no buttons, but uses cameras and sensors to understand its position in space, and provides user feedback in the form of vibration, lights, and sound. The scanning device incorporates a fiducial marker/s or embossing or locator bump 1101 to ensure correct placement in device user's hand. In one mode of the embodiment, the scanning device is used by the device user, in another mode of the embodiment, the scanning device is placed on a surface such as the subject's hospital bed and is used as a passive scanning device—recording observations while traditional manual observation is performed by the device user. In this embodiment, the scanning device has sensors 1103 on the top and bottom sides of the device, these sensors including but not limited to moisture, gas, infrared (spot and spread, contact and non-contact), terahertz (sub dermal), impedance, range, proximity, and orientation. Finally the scanning device incorporates wireless charging, such that the scanning device's full surface is easy and able to be cleaned with standard wipe-down chemicals used in a typical cleaning cycle in hospitals to avoid cross contamination.

One embodiment of the present invention includes a hand-held scanner for evaluating a pathogenic bio-signal anomaly in a patient that includes a cylindrical housing sized to be hand-held, an optical sensor, a proximity sensor, and a location processor electrically connected to the optical sensor and the proximity sensor and enclosed in the housing to use a combination of data from the optical sensor and data from the proximity sensor to localize the hand-held scanner in relation to the patient and to the pathogenic bio-signal anomaly. The cylindrical housing may include all types of cylindrical shapes including circular, elliptical, parabolic, and hyperbolic.

Figure 12:
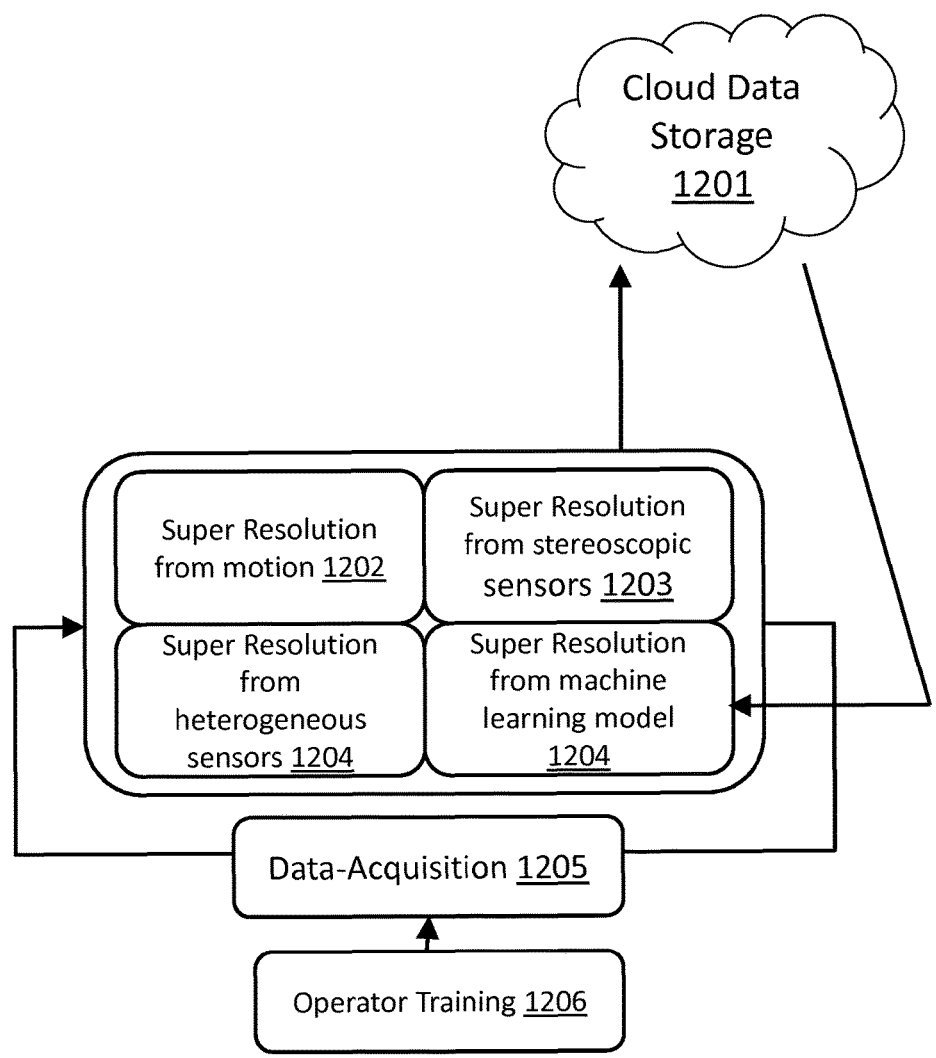
FIG. 12 illustrates different ways of generating super-resolution infrared images using combinational techniques to enhance low-resolution IR sensors and other sensors to achieve superior image processing.

One aspect of sensor fusion as discussed above is the creation of super-resolution images by using multiple types of data sources. FIG. 12 shows a schematic of different ways of producing these images, using motion 1202, cloud data storage 1201, heterogeneous sensors 1204, stereoscopic sensors 1203 and feature matching based on higher-order image features determined using machine learning 1204. Data may also be provided via data acquisition 1205 and operator training 1206.

Figure 13:
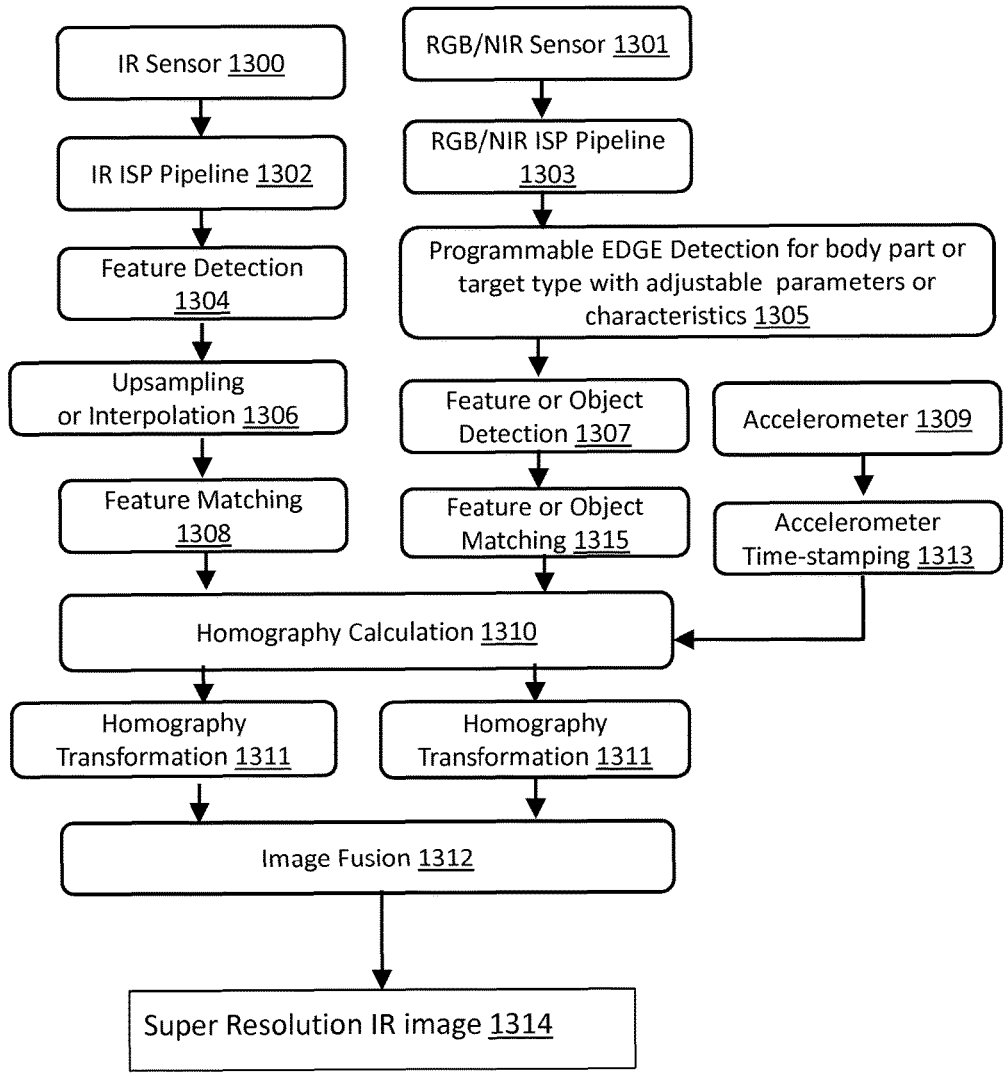
FIG. 13 illustrates one embodiment of the methods in FIG. 12, a data capture pipeline for heterogeneous sensor super-resolution with automated gain control (AGC) and camera stitching.

In an embodiment of super-resolution from heterogeneous sensors 1204 that includes the use of motion 1202, diagrammed in FIG. 13, an infrared super-resolution image 1314 is constructed by the scanning device using a sensor fusion approach between a visual-light or near-infrared light sensor or camera 1301 and an infrared sensor or camera 1300. Super-resolution, as one skilled in the art is aware, is the process of synthesizing images with higher pixel resolution than the underling sensor capability by tracking incremental motion of the sensor and using images captured at inter-pixel distances to "fill in" inter-pixel data. In the normal case of visual images, image-to-image alignment is performed via feature or object matching 1315 between successive images. In this embodiment, as the feature density in the infrared data may not be high enough to allow adequate feature matching, the incremental alignment of the visual image is used to augment the infrared image. The following flow describes this process in detail. Infrared image data is captured by the IR Sensor 1300, with simultaneous capture of visual image data by the RGB/NIR Sensor 1301. IR and visual image data frames are processed by their separate ISP (Image Signal Processing) stages 1302, 1303 and feature detection 1304 is run directly on the IR image data. Visual image data is processed using a customized, programmable edge detection algorithm 1305 to identify the visual image as belonging to a specific limb, body part, or region on the subject. At this point feature detection 1307 is executed on the visual image. As the Infrared image data is likely at a different resolution than the visual image, at this stage in the processing up-sampling or interpolation 1306 is used to equalize the image resolution between the two pipelines. A homography calculation 1310 is performed on the image data using accelerometer 1309 and accelerometer time-stamps 1313 to align identified features in the image data, homography transformations 1311 are performed on one or both of the images, and image fusion 1312 is accomplished based on the resulting transformed image. The output of this process is a super resolution infrared image 1314 suitable for processing by the system.

In another embodiment of the super resolution approach from FIG. 13, image-to-image alignment is performed via an alternate approach to feature detection 1307 and Feature or object matching 1315 between successive images, the embodiment using higher-order objects that are determined and subsequently recognized using the output of a machine learning algorithm. In this embodiment, previous image data is used to train a machine learning algorithm to recognize higher-order objects such as but not limited to an anatomical features or regions of the subject. Once training has been completed, the real-time images are processed by the machine learning algorithm to recognize the presence and location of objects in the visible realm. These objects are used in subsequent stages of the image-processing pipeline in a similar manner to how lower-order features are used.

Figure 5:
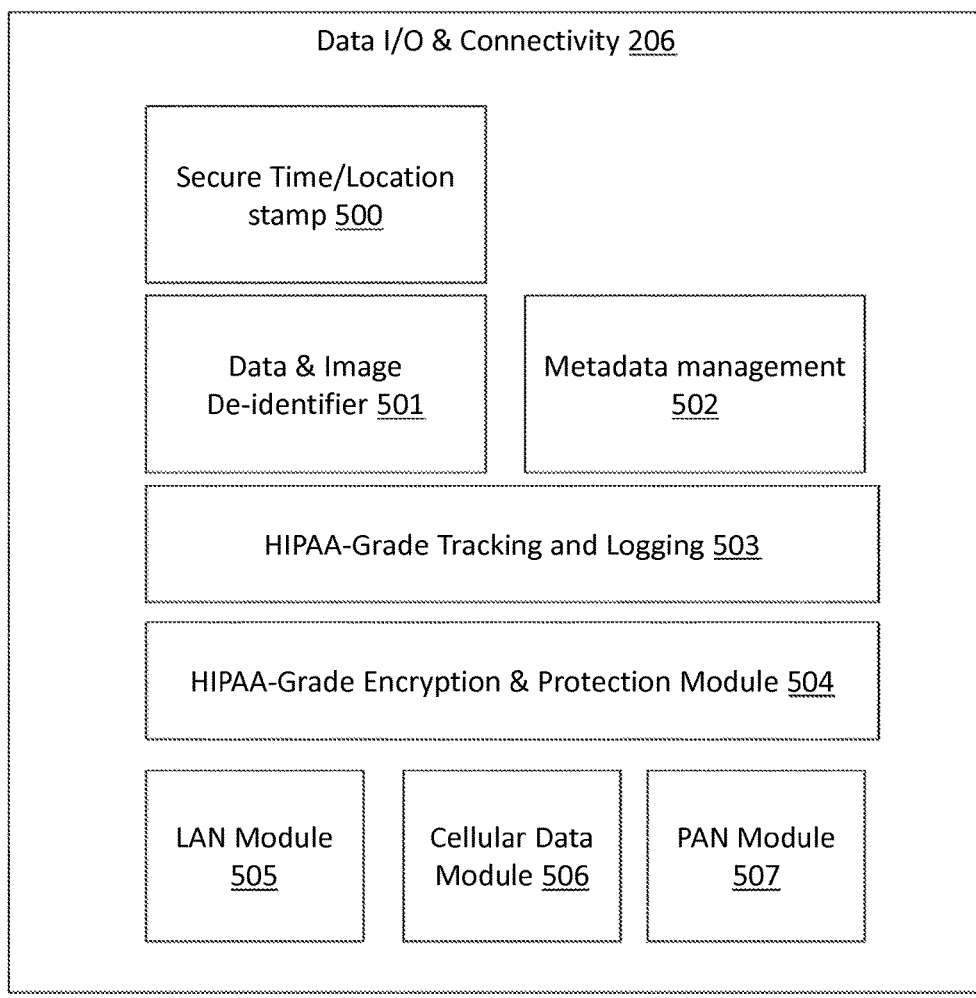
FIG. 5 illustrates in more detail the data input/output module of the scanning device, which controls data storage formats and transmission of resulting data to the server system.

FIG. 5 illustrates the data input/output (IO) and connectivity module 206 of the scanning device. This module is responsible for translation of sensor data into compact, encrypted storage formats, which will be discussed below, HIPAA-compliant secure storage of the patient data, and secure transmission of patient data, to the server system via various transmission mediums. Specifically, this module is comprised of a secure time and location stamp module 500, which attaches a time stamp and location stamp to patient data that can subsequently be verified accurate by the server system, in one embodiment using a mobile-device-friendly light-weight implementation of NTP (Network Time Protocol) between the server system and the module, where traffic generated in the protocol is cryptographically secure to guard against man-in-the-middle attacks. Furthermore, the module is comprised of a data and image de-identifier 501, which protects subject identity while the data is in the scanning device, during transit between the scanning device and the server system, and during storage in the server system. In one embodiment, the data and image de-identifier substitutes a globally unique ID (GUID) for the subject identity for processing within the system, allowing the subject GUID to be associated back to a real subject identity at appropriate points in the server system. In this way, the system is guarded against subject privacy breaches (HIPAA data breaches), in the case where the physical security of the scanning device or server system is compromised. The module further is comprised of a metadata management module 502, which translates biosensor data into more compact and encrypted formats, one embodiment of which will be described in more detail below. The module is furthermore comprised of a HIPAA-grade tracking and logging module 503 that generates data access and manipulation logs suitable for compliance with HIPAA data security standards. The module is furthermore comprised of a HIPAA-grade encryption and protection module 504, which encrypts data for storage and transmission. In one embodiment, the encryption mechanism uses the NIST-recommended AES-256 symmetrical encryption algorithm for encrypting data at rest and NIST-recommended transport layer security (TLS) 1.2 for data in transit. Furthermore and finally the module is comprised of multiple data transport mechanisms, including but not limited to LAN/WLAN 505, cellular data 506 and personal area network (PAN) modules 507. These modules transport data and metadata from the scanning device into a local area network, wide area network, personal area network, or cellular network, ultimately providing connection to the server system.

In one embodiment of the metadata management module, the module translates captured bio-signals to compact encrypted metadata (BioSM) that can be stored, transmitted and analyzed in real-time on low power compute devices, due to its ability to represent the essential information in the original bio-signals in a more compact form than the original bio-signal format. In one embodiment, The BioSM format is similar to .jpeg extensions but created uniquely for storing key bio-signals, scores and other measurements, including time stamp and location stamp, and references linked & other particular images or similar output from the sensor arrays and is encrypted and CRC protected. The BioSM also can store and protect the key factors (KF) and key indicators (KI) for each calculation, patient, scan, time slice or physical location. In one embodiment, there are two encrypted instances stored—one where the customer can decrypt (BioSM1), and one version which they cannot, the latter being used for escrow purposes (BioSM2) suitable for a third external party to have control of. In one embodiment, the BioSM1 can be interrogated, (when suitable encryption keys are available), viewed and manipulated in near to real time on low power CPUs—alleviating the need for large data file transfers or transmission of sensitive patient identifiable data. In some cases the use of BioSM alleviates the need entirely to store or transmit any primary data out of the scanning device, when analysis of the BioSM can be accomplished completely on the scanning device itself—enhancing privacy and other security, and providing anonymity where required or desired.

Figure 6:
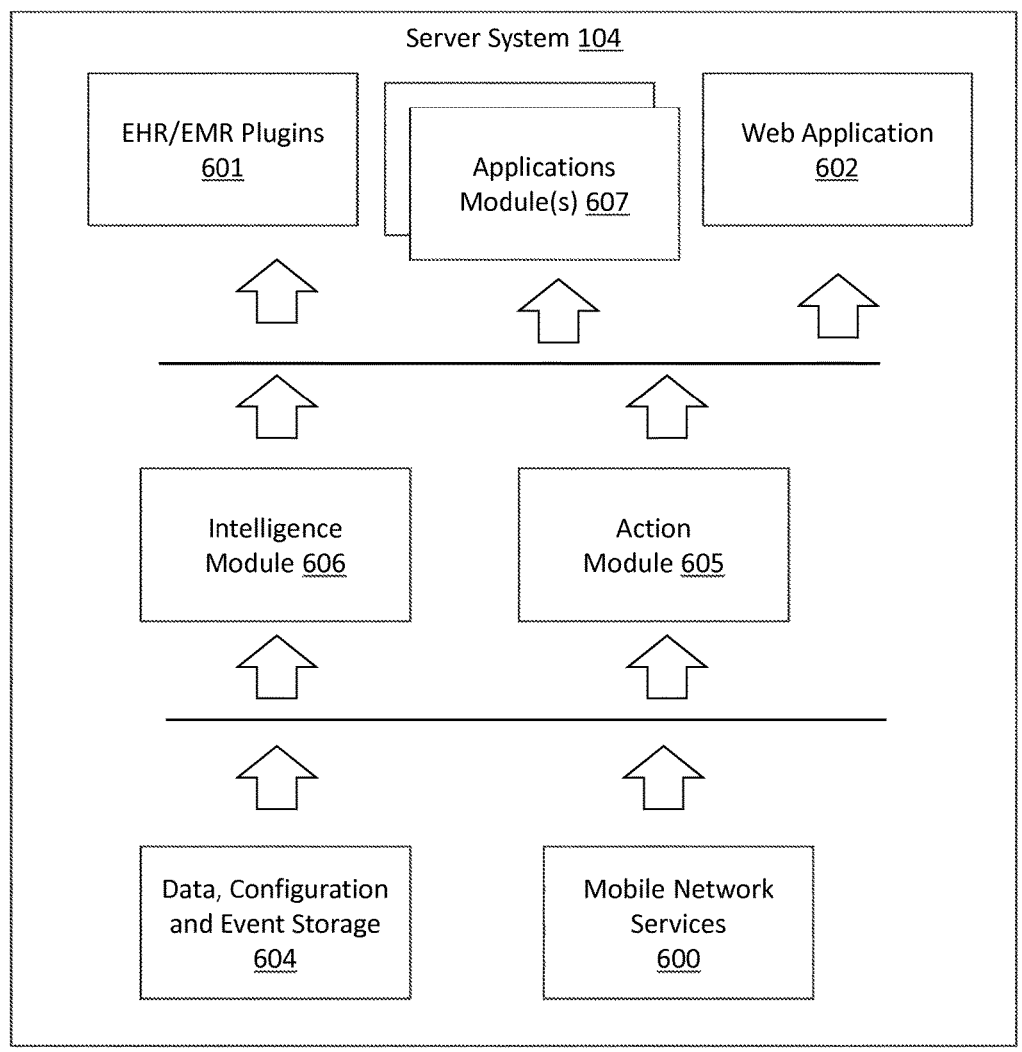
FIG. 6 illustrates the system-level details of the server system, including data storage, mobile services, data analytics, web application, and other important functional or logical blocks.

Furthermore in regards to the embodiment of escrow-able data format (BioSM2), the format allows the storage of subject data, including but not limited to skin incidents, by use of encryption key management, time and locations stamps and bio-signals and key inputs. The benefits of using such an escrow system include:

Boosts legal defensibility by enabling unique, secure documentation and data record system
Allows non-alterable, non-tamperable, court-evidence-worthy storage of
Historical images and other sensor data
Metadata
Treatment plans//results
Audit logs and transaction records
Provides user-defined discoverability/archives FIG. 6 illustrates in more detail the internal composition of the server system 104. The server system is comprised of multiple modules, including the data, configuration and event storage module 604, which enables HIPAA-level-private and encrypted storage of subject data, including but not limited to sensor bio-signals and their derivatives, metadata including but not limited to demographics or historical data concerning the subject such as diagnoses and medical history, and data concerning the subject's physical environment, either current or historical. The server system is furthermore comprised of a mobile network services module 600 which is responsible for establishing and maintaining network connections to scanner devices, including uploading subject data generated by the scanning device's Data I/O connectivity module 206, and conveying data generated by the system back to the scanning device via the network connection. In one embodiment, the module is implemented using a REST (Representational State Transfer) API encrypted using HTTPS and secured with authentication (login) and authorization (access rights). Furthermore in one embodiment, the module will use APNS (Apple Push Notification Services) or GCM (Google Cloud Messaging) to allow asynchronous notifications or data to be delivered to the scanning device, which in some embodiments are located on mobile networks.

The server system is further comprised of an EHR/EMR Plugin module 601 to allow information generated by the system to be integrated into existing medical and health records system, such as but not limited to those developed by Epic Systems Corporation, and AllScripts. Furthermore the server system is comprised of a web application module 602, which communicates information to other users in the system 105, 106, 107 by means of a web browser such as Chrome, Internet Explorer or Safari. The server system is furthermore comprised of an intelligence module 606, which analyzes information generated by the system, and an action module 605, which generates actions, events or alerts from the bio-signals or their derivative information.

Figure 7:
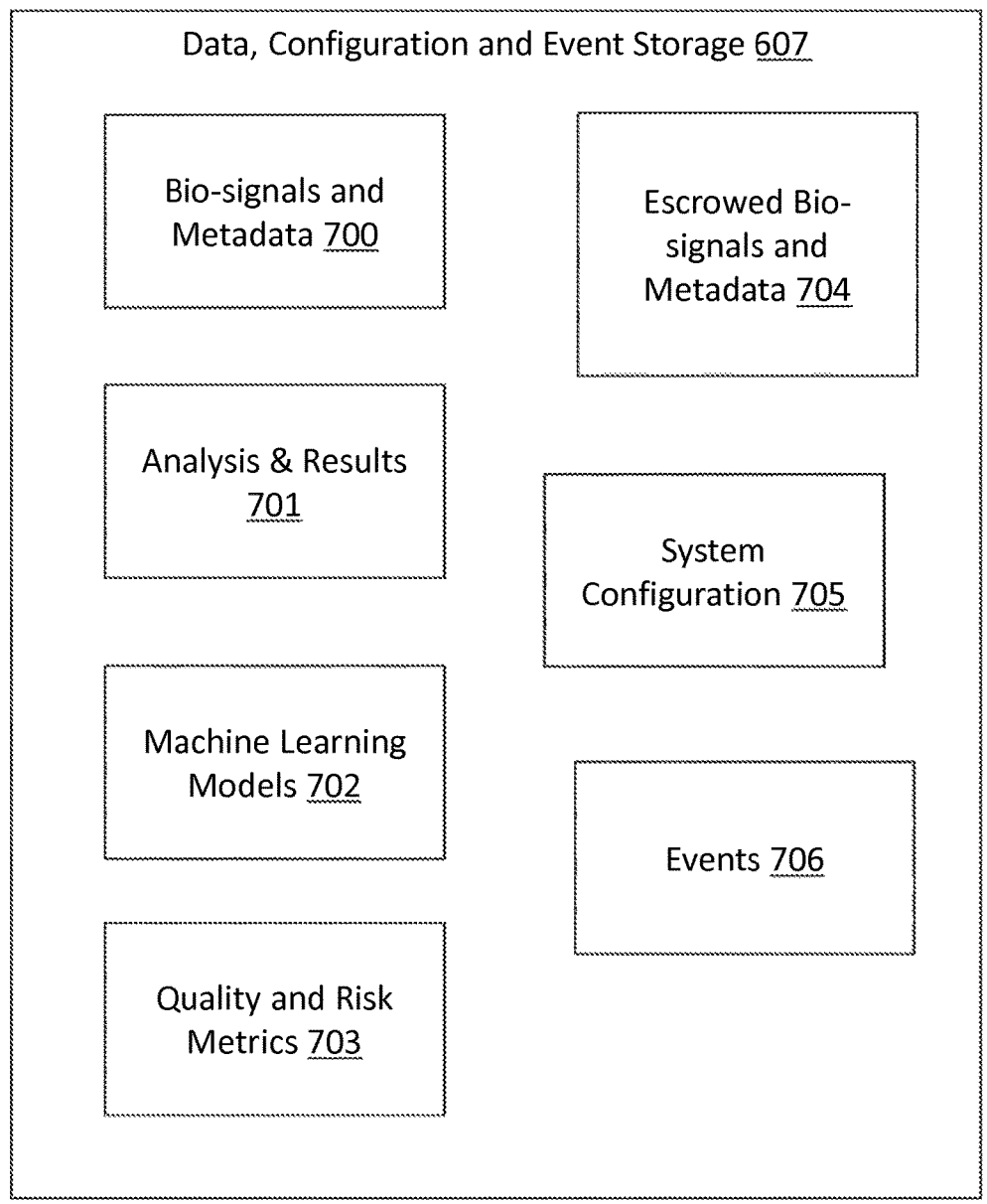
FIG. 7 illustrates in more detail the data, configuration, and event storage module in the server system, including the types of data that are stored in the system.

FIG. 7 illustrates the data, configuration and event storage module in more detail. The module stores bio-signals and metadata 700, system configuration 705 pertaining to a subject 100, group of subjects, users of the system 105, 106, 107, device users 102, or groups of these users where these groups could be defined and managed by the system itself or a client of the system. System configuration could include, but is not limited to active session information, location, authorization (access rights) or authentication status, group membership, responsibilities within the system, or other configuration information. The module also stores events 706, where an event is defined as an actionable message, notification, functional logging entry, audit logging entry, analytics event, or other entity that is generated by the system during the course of operation. The module stores other information generated by the intelligence module 606, including analysis and results 701, machine learning modules 702 and quality and risk metrics 703. The module stores and retrieves these information types, as well as a caching, archiving, backing up, and restoring the information types as part of the general operation of the system. In one embodiment, this module is implemented as a noSQL database such as CouchDB or MongoDB, with a Memcache in-memory distributed cache, and an Amazon S3 (Simple Storage Service) archiving service, but could also be comprised of other similar technologies including an SQL database technology such as MySQL.

In one embodiment, the BioSM and BioSM2 data formats are used to store bio-signals and metadata 700 and Escrowed bio-signals and metadata 706 in this module. In another embodiment, the data, configuration and event Storage module provides a computer-accessible database and repository containing the associated bio-sensors and metadata, calculated key factors (KF) metrics, measurements and indices involving skin injury interception, skin integrity status, pathophysiological conditions manifesting in skin alterations and skin early warning score (SKEWS), thereby providing a proprietary collection of volumes of data about patients and their skin, which has not been possible with the databases currently used for healthcare evaluation which are not capable of storing an generating the SKEWS an novel bio-signal inputs (pre-cursor signals/bio-signal signatures) of this invention. This embodiment enables data to be analyzed and aggregated to understand trends in injury and/or underlying pathophysiological condition interception, addressing such issues as which skin conditions go on to heal with what specific interventions (efficacy), establishing normative data on timelines to recover, and development of validated clinical best practices for treatment. Ultimately this embodiment cross-references skin properties vs. injury and relevant pathophysiologic conditions, in order to intercept injuries at the earliest possible opportunity.

Figure 8:
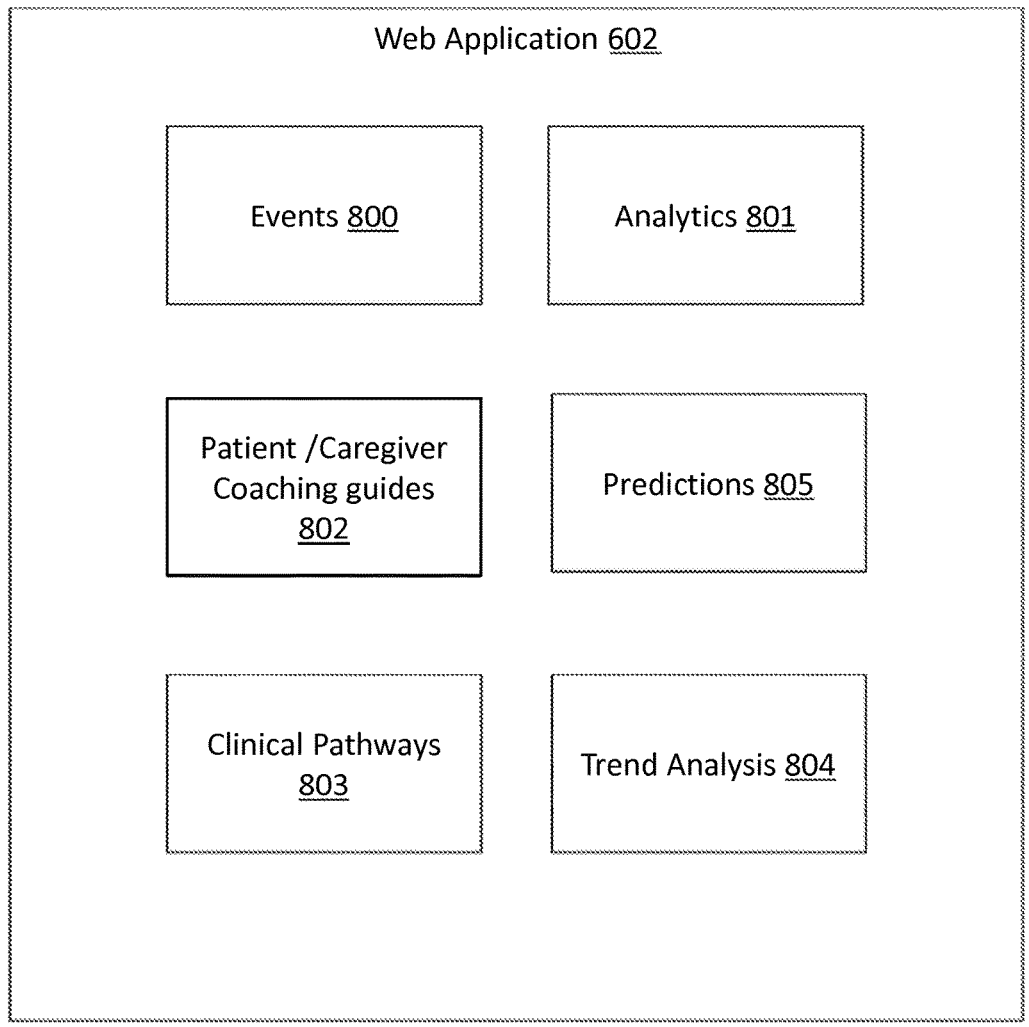
FIG. 8 illustrates in more detail the web application module in the server system, showing the types of information that are conveyed to users of the system.

FIG. 8 illustrates the web application module 602 in more detail. The module allows the system to display information and allow interaction with the system for users 105, 106, 107 via a web browser such as Chrome, Internet Explorer, or Safari. In one embodiment the module uses web platforms and technologies including RoR (Ruby on Rails) web application framework, HTML (Hypertext Markup Language) the JQuery JavaScript framework, and the HTTPS transport (Secure Hypertext Transfer Protocol) to provide information access and interactivity. The module provides access to various types of information in the system, including events 800, patient/caregiver coaching guides 802, clinical pathways 803, analytics 801, predictions 805, and trend analysis 804.

In one embodiment of the web application module, the system provides real-time and auto-populated skin surveillance monitoring via graphical electronic dash-boards with wide ranging flexible data display options programmable by the end-user. The module would allow customizable skin incident and/or condition severity monitoring (including but not limited to patterns of latent pathogenic bio-signal anomaly captured by the device and not otherwise readily accessible via contemporary clinical assessment methods), messaging and reporting, with or without required user intervention. The user interface would be customizable and programmable, where options would exist for the user to pick a "plug and play" display module from a master list of display modules to be added to their view of skin incidents, and would show the information types listed above 800-805. These modules could include but are not limited to displaying information by geo-locale, such as by hospital or medical facility floor, hall or department, and by time, including by worker shift, or day or other time period. In all cases the customizable modules could be displayed at user-programmable locations on the web application dashboard.

Figure 9:
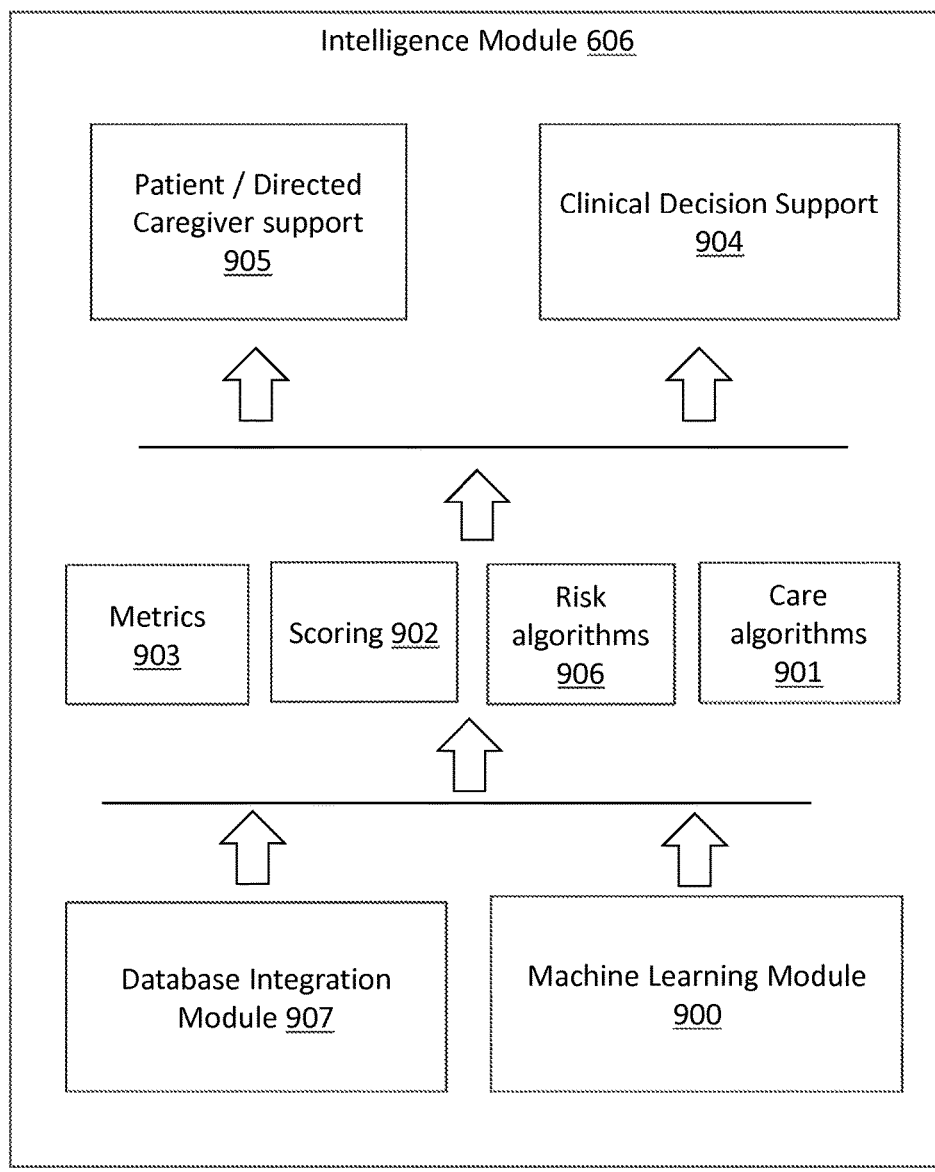
FIG. 9 illustrates in more detail the intelligence module in the server system, including the types of algorithms and machine learning models that are developed and used in the system.

FIG. 9 illustrates in more detail the Intelligence module 606, which performs analysis on subject bio-signals, signals from the subject's physical environment, input and feedback from users of the system, and information derived from them by the system. The module encapsulates multiple core technologies that are used to generate or synthesize meaningful, actionable information from data captured by the scanning device, from external medical, clinical or health-related public and private databases, and from input from users of the system. The Intelligence module includes a machine learning module 900, which leverages pattern recognition and computational learning theory, a subfield of artificial intelligence, to generate algorithms that can learn from and make predictions on data derived from these sources. The algorithms developed fall into two general categories, care algorithms 901 and risk algorithms 906. Care-driven algorithms are developed and executed on bio-signals from the subject or their physical environment, and machine learning models are trained and executed to recognize patterns in the data that represent injury or inflammatory condition, where injury is indicated by any acute or chronic episode of soft tissue pathology where bio-signal patterns, bio-markers or other identifiable elements or references would deviate from baseline; where inflammatory condition is indicated by any acute or chronic episode of rheumatoid disease process where bio-signal patterns, bio-makers or other identifiable elements or references would deviate from baseline. Ultimately the end-result of such analysis is to improve subject outcomes where injury or inflammatory condition is identified. The actual models used for care-driven algorithms include but are not limited to supervised learning models such as CNNs (convolutional neural networks), traditional neural networks, random-forest models, and traditional stochastic models, such as logistic regression. Risk-driven algorithms are developed and executed on operational data, including user input, bio-signal metadata, and external database input to generate operational models that are focused on reducing cost, reducing risk, or increasing gains or efficiencies in the application of care, allocation of resources, or other operational needs of the customers of the system. The actual models used for risk-driven algorithms include but are not limited to supervised learning models such as CNNs (convolutional neural networks), traditional neural networks, random-forest models, and traditional statistical models using logistic regression. In both cases, unsupervised learning algorithms are used to pre-process input data, perform data dimensionality reduction, and in some cases perform deep learning. In one embodiment, the machine learning module is implemented as a distributed system capable of executing models implemented in Python or R, two popular programming languages in this domain. The system is distributed such that individual servers in the distributed cluster can run versions of the algorithms in parallel on multiple streams of input, such that many operations can be run in parallel. In an embodiment, this system is implemented by BDAS, the Berkeley Data Analytics Stack, an open source software stack that integrates software components used to implement systems that process Big Data. In other embodiments, custom components are used to implement the distributed machine learning module.

Additionally, the Intelligence module includes a database integration module 907 that normalizes data from external databases for use within the system. External databases can include but are not limited to medical, clinical, demographic, cultural, or other databases that are publically available or privately made available to the system to provide richer context for data that is captured by the system.

Data from the database integration module and the machine learning module are integrated at a higher level into scoring 902 and metrics 903 modules. The scoring and metric modules create custom representations of injury, care practices, risk mitigation practices, and other data gathered by the system and/or integrated with external data that are intuitive, easy to understand by system user's and reflect the state of the art in representation. The ability to integrate external data into the scores and metrics ensure that the system is constantly and consistently working with the state-of-the-art data and practices. The resulting scores and metrics are conveyed to users of the system, and in some embodiments may be released back to the public domain to further industry understanding and improve the state of the art in data, practices, and understanding.

Algorithm results, scoring and metrics are fed into patient/directed caregiver support 905 and clinical decision support 904 modules. The clinical decision support module increases quality of care, enhance health outcomes, help to avoid errors and adverse events, improve efficiency, and reduce costs for customers of the system. Similarly, the patient/directed caregiver support module specifically adjusts subject care upon determination that an injury or potential injury exists.

Figure 17:
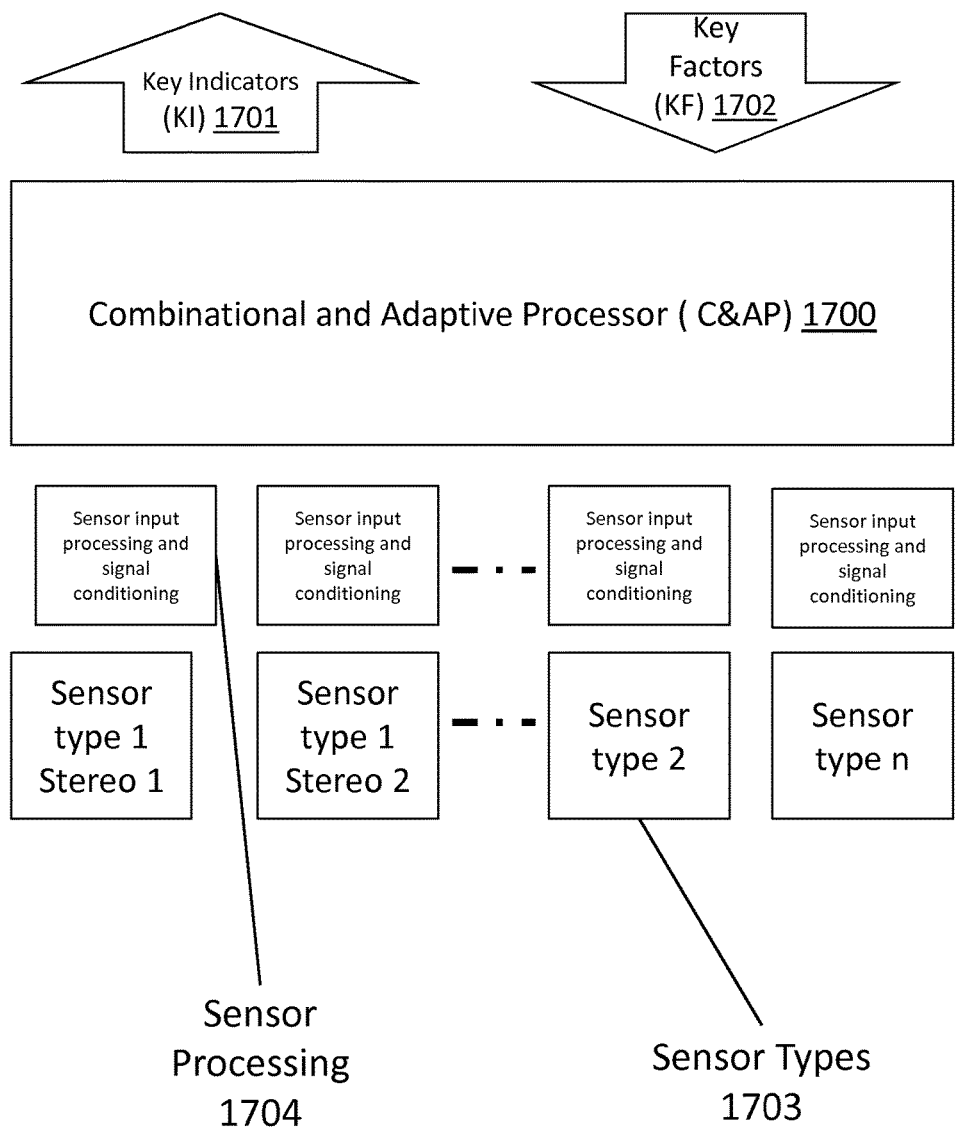
FIG. 17 illustrates an embodiment of taking dynamic input from an large array of multiple real-time sensors used to scan the skin provide key indicators (KI) of presence of impending injury/condition or to track an existing injury/condition.

One embodiment of the metrics module, as illustrated in more detail in FIG. 17, includes a combinational and adaptive processor (C&AP) 1700 taking dynamic input from a large array of multiple real-time sensors used to scan the skin and provide key indicators (KI) 1701 of presence of impending injury/condition or to track an existing injury/condition. In this embodiment, C&AP 1700 performs skin matching, skin texture analysis, temperature profiles, SLAM, intelligence skin location identification, reflection and color analysis, sizing and location, environmental temperature, and range determination, and derives "key indicators" (KI) 1701 primed by key factors (KF) 1702, and utilizing machine learning to improve accuracy.

In this embodiment, sensor types 1703 may include but are not limited to:
- Mono and stereo visible and infrared cameras
- Infrared pile or spot measuring
- Ambient temperature and ambient light measurement
- Gas sensing, ultrasound, light sensing technology (NIR) to see blood vessels under the skin
- Gyros and accelerometers
- GPS/Wi-Fi and other location aware sensors
- Depth sensing sensors
- Bar or patient ID scanning
- Terahertz sub-dermal scanner
- Ultrasound scanner
- Impedance spectroscopy
- Gas sensors
- Moisture sensors Key indicators (KI) include, but are not limited to:
- Bio-signals (including inflammation, pH, skin/tissue temp, electrical impedance, odor, moisture, spectroscopy measure of deoxy-/oxy-hemoglobin levels, and chemical concentrations)
- Temperature profile, Temp differences, Temperature comparisons (including between different skin scan samples at ipsilateral or contralateral limbs and/or mirror images of a region of interest (ROI) of the same patient or patient to comparable reference populations)
- Color indicators, color gradient indications
- Reflectivity indexes
- Texture indexes
- Area, areas interest, volume, contour heights, intensity, gradation, profile
- Key performance markers
- Key indicating factors Key factors (KF) include, but are not limited to:
- Data from EHR
- Patient profile
- Key ratios and trigger points for adaptive logic
- Priming function for Adaptive logic
- Override parameters from system users or administrators One embodiment of the present invention includes a monitoring system for early detection of a latent pathogenic bio-signal anomaly in a patient comprising an array of multiple real-time sensors and a metrics module. The metrics module includes a combinational and adaptive processor and memory, to receive one or more key factor input for the patient, acquire and store sensor data from the multiple real-time sensors, determine a combination of the sensor data from a subset of the multiple real-time sensors to use based on the one or more key factor and the sensor data from the multiple real-time sensors, generate a key indicator to represent skin health that is a weighted function of the combination of the sensor data from the subset of the multiple real-time sensors and the one or more key factor, and compare the key indicator to a baseline of key indicators to determine if the latent pathogenic bio-signal anomaly is present.

The baseline of key indicators can be a population key indicator baseline, that is, a baseline derived for a group of patient. They baseline may also be an individual baseline. For example, a baseline for the patient previously.

One embodiment of the scoring module performs automated and quantified skin and wound assessment, using parameters and analytic processing, with localization and anatomical referencing onto individual patients. The embodiment may automatically calibrate and automatically capture skin integrity status, pathophysiological/inflammatory condition status and wound parameters. In this embodiment, wound and condition parameters may include but are not limited to:
- Measurements—Length, Width, Depth
- True contour mapping, including
  - What's raised
  - What's depressed
- Skin/Wound Bed—tissue color, tissue type/viability
- Exudate—amount, consistency/viscosity, odor
  - Quantity validated relative to wound size/volume
- Wound Edges—quality, texture, irregularity, callous, epibolized/rolled
- Periwound—maceration, erythema, induration, excoriation/denudement, weeping
- Localization and placement technology to "locate" in the future—anatomical referencing
- Tissue deformation mapping, biofeedback Another embodiment of the scoring module creates a physiological score based upon distinct, strategic and machine learning from "bundling" of automatic measurement of skin, and tissue bio-signals using computer imaging & analytics, called the skin early warning score (SKEWS). SKEWS provides early warning of underlying conditions or complications, helps monitor skin and improve how quickly a patient experiencing clinically meaningful changes in skin condition receives care. SKEWS is suitable for bedside, self-monitoring, rapid skin surveillance and can provide a single, easily-communicated (for example 1 is good 5 is bad) score or measure to junior staff members such as nurses' aides or family members to trigger immediate action or follow-up if a stated or directed threshold is reached. For example a Family member could be directed by a doctor to call them if a Score a 3 was indicated.

Examples of SKEWS include but are not limited to SKEWS via LE Vascular Screen:
- Pedal Pulses
  - Dorsalis Pedis,
  - Posterior Tibialis
  - Absence or presence
- Capillary Refill—n=<3 s
- Doppler Wave Form
  - Monophasic, biphasic or triphasic
- Venous Filling Time, n=b/w 10-15 s
- Dependent Rubor, post 2 m
- ABI and TBI screening
- Biofeedback for manual skills training Another example of SKEWS would provide a method of quantifying severity, progression and chronicity of an inflammatory type reaction or underlying pathophysiological/inflammatory condition.
- Patch Testing
- Skin Prick Testing
- SCORing Atopic Dermatitis (SCORAD)
- Psoriasis area severity index (PASI)

FIG. 18 shows a specific embodiment of SKEWS. In this embodiment, the SKEWS scoring method includes an additive combination of assessment criteria to arrive at the final score. In this embodiment, the individual assessment criteria includes the following components:

Risk profile for Injury/Wound Development, such as the Braden Risk Assessment 1801
Condition/Injury/Wound, Periwound, Wound Edge &/or ROI Skin 1802
  Biosignal Signature (assigned metric/score)
  Biosignal absence, presence (assigned metric/score)
Wound/Injury/Condition Dimensions 1803, including
  Length, Width and Depth, and Height
  Undermining
  Tunneling
  Total Body Surface Area (Metric)
Peri-wound/-injury/-condition Status 1804, including evaluation of tissue type or quality, which may be one of
  Intact
  Macerated
  Erythematic/Inflamed
  Indurated/Firm
  Excoriated/Denuded
  Color
  Temperature (Cool or Warm)
Wound Bed Status 1805, including evaluation of tissue type or quality, which may be one of
  Epidermis
  Dermis
  Granulation
  Necrotic Tissues (Eschar, Slough)
  Muscle/Tendon/Bone/Ligament
  PUSH Score
Wound Edge/Margin 1806, including evaluation of quality and characteristics, which may be one of
  Attachment
  Definition (regular, irregular)
  Epibolized
  Hyperkeratotic
  Fibrosed
Results from Noninvasive Vascular Tests/Screens 1807, including
  Pulse (Dorsalis Pedis or Posterior Tibialis)
  Capillary Refill
  Blanch Test
  Rubor of Dependency
  Venous Filling Time Test
  Ankle Brachial Index To calculate the SKEWS score, a sub-score 1808 (zero to five, where zero represents no risk and five represents an active injury, with risk increasing relative to subscore 1810) is assigned to each component 1801-1807. These sub-scores are added together to create a SKEWS score 1809 (zero to thirty-five, where discrete risk categories are assigned to ranges of values, for example the range zero to six representing no risk, and the range twenty-six to thirty-five representing severe risk 1811).

Figure 10:
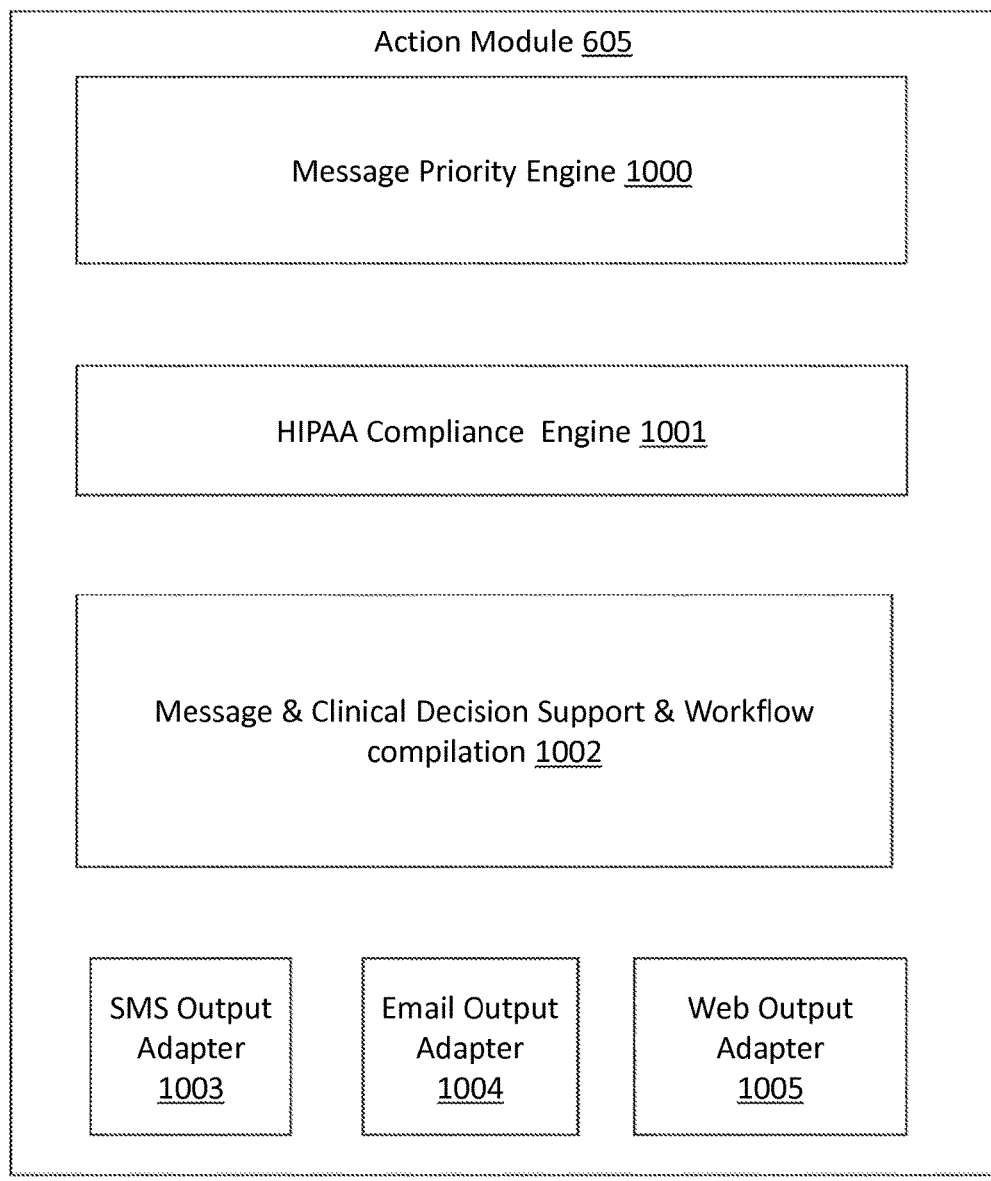
FIG. 10 illustrates in more detail the action module in the server system, including the types of events and event delivery mechanisms that are used in the system.

FIG. 10 illustrates in more detail the action module 605, which organizes, prioritizes and sends messages, events and other notifications in compliance with HIPAA privacy guidelines. The module includes a message priority engine 1000, which implements a message importance hierarchy based on specific care guidelines and other rules. In one embodiment, the message priority engine maintains a normal priority message queue and a high priority message queue. Messages generated by the system will be placed in one of these queues based on specific care guidelines, content or intrinsic importance of the message, intended individual recipient or intended group recipient. In this embodiment, the high priority message queue is processed completely, or drained of messages, before the normal priority queue is processed, thereby guaranteeing that all High priority messages are processed before normal priority messages. The module includes a HIPAA compliance engine 1001 that ensures that messages do not include personally identifiable information as per the HIPAA definition. In one embodiment, this is implemented by forming a first message that indicates to clinical, QRM or other user, or device user that an externally unidentified action needs to take place for a particular subject, without revealing what specific action is required. The HIPAA compliance engine would then form and store a second message with specific subject identification and specific action required. To act on the first message, the clinical, QRM, other or device user would be required to authenticate with the system, whereby the system would validate the identity of the user, as well as validate the authentication (access rights) allowed by the user, ensuring that said user was authorized to see the content of the second message and act on behalf of the information therein. The action module further includes a message & clinical decision support & workflow compilation module 1002, which integrates clinical, workflow, or other context into the second message content based on output from the intelligence module 606. Finally, the action module contains output adapters such as but not limited to SMS 1003 email 1004 and web 1005 output adapters. The SMS and email output adapters would use a mapping between a user and their mobile network device (e.g. cell phone or other mobile device) or email address to route the first message to a specific user. The web output adapter would provide access to near-real-time messaging using existing message delivery technologies such as XMPP (Extensible Messaging and Presence Protocol), HTTP Long Polling, Secure Web Sockets, or other asynchronous message delivery technologies used in the state of the art.

FIG. 6 shows the application module(s) 607 component of the server system 104. Application modules create and deploy large-scale server-based applications, which incorporate business logic, user interface, network connectivity and data storage by leveraging the components of the server system that provide these services 600-606, along with providing application-specific services themselves. In the preferred embodiment, an instance of an application module would be implemented as a stand-alone, scalable server cluster that allows interaction with said server system components using a service-oriented architecture (SOA), implemented in terms of application programming interface (API) technology such as REST (representational state transfer) or SOAP APIs, whereby application-specific functionality is available to the system via access to these APIs. As shown in FIG. 6, one or many application modules can be running independently and in parallel in the preferred embodiment.

In one embodiment of a scanning device application module 207, the application module ensures low user error rate in skin and tissue scanning involving IR and visible light in a clinical setting through training, targeting, real-time checking, validation and feedback. In this embodiment, device user training uses demonstration video presented externally from the scanning device, then, putting the scanning device into a training mode, measures success of user understanding and competence by matching the hand movements to the required sequences by Sensors within the scanning device, such as gyro and accelerometers. In this process, a bio-signal capture event is not enabled or registered unless the scanning device orientation is correct and the target of the scanned area matches the expected location, thus intelligently recognizing the sequence and location and limb type and also recognizing if scans are attempted in incorrect order.

Figure 21:
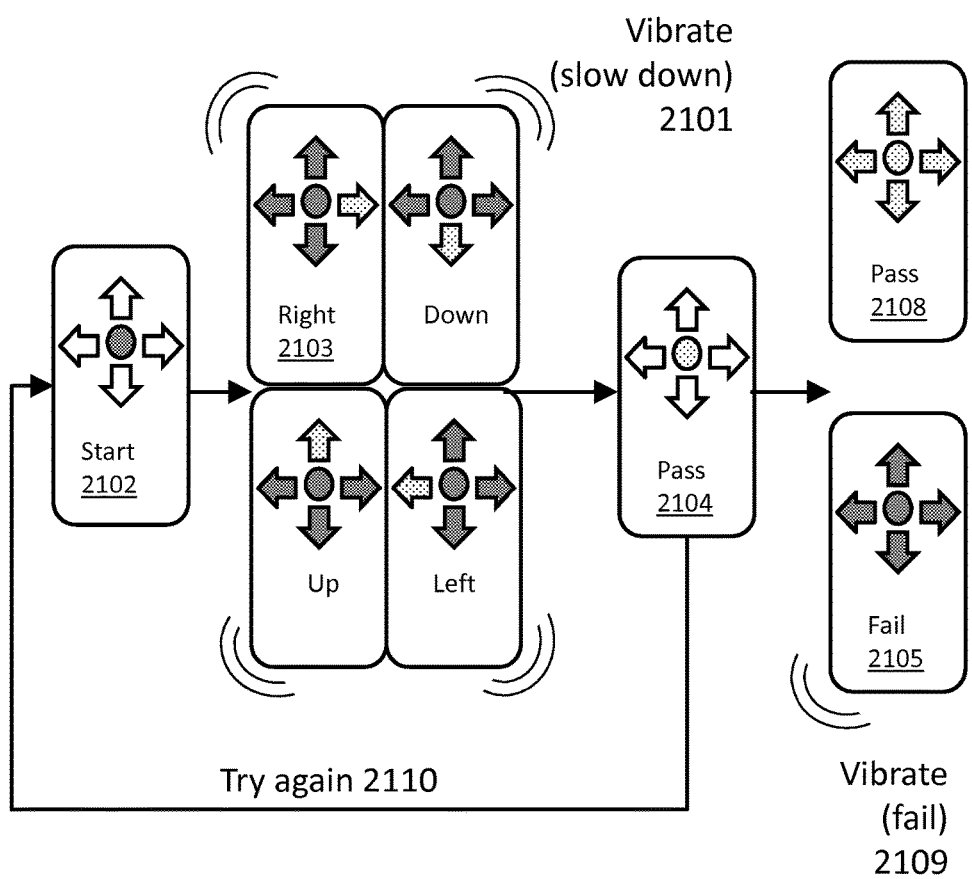
FIG. 21 shows an example of a projected capture user interface of the present invention.

In this embodiment, shown in FIG. 21, light projection onto the skin can also confirm scanned area, and feedback of a correct scan can be indicated by changing the projected light color and shape, and by vibrating the scanning device. Other embodiments could use other output such as emitting a confirmation sound, updating a user interface element, or the like to register successful or unsuccessful capture. In this embodiment, the device user starts the scanning process 2102, with a red symbol output conveying that the scan process is starting. The scanning device then guides the device user to move the scanning device in the correct direction via colored arrows projected onto the skin 2103. At any time the device user moves the scanning device too fast, the scanning device will vibrate 2101 notifying the device user to slow down. Once the movement required to complete the scan is complete, the scanning device projects a green symbol signifying that the scan has passed initial requirements 2104, and post-processing is occurring. Post-processing success 2108 is signified by projecting all green symbols, and failure 2105 is signified by projecting all red symbols and vibrating the scanning device.

Correct distance of scan can be ensured by light sources such as pico-projectors or other structure light or spot light devices pointers or sound—dramatically improving targeting success rate. Furthermore, a scanned image is quality-checked against local database to allow feedback, for example, in one embodiment rapid checking could determine successful or unsuccessful bio-signal capture within 500 ms, which would provide near-instantaneous feedback to the device user.

In another embodiment, feedback to the device user uses display blink-rate and direction combined from 3 control loops
    High-rate gesture based loop based on accelerometer for near-instantaneous feedback;
    Lower-rate image-quality based loop based on correspondence between IR and RGB/NIR sensor feature points, providing intermediate-level feedback;
    Lowest-rate loop based on machine learning model data, providing long-term feedback.

In another embodiment of a scanning device application module 207, the application module provides a Data Capture Training system. In this embodiment, the training system teaches operators how to operate the scanning device user-interface by simulating multiple capture scenarios with various subject scenarios, including subject at rest or in motion, or agitated. In this embodiment, the system learns "good" gestures based on accelerometer for high quality data-capture, using metrics such as objectively measured image quality and time to capture. Longer-term feedback is provided by performing statistical analytics on a multitude of training sessions with different device users, or by comparison to models based on deep learning, which learn how to train operator to use correct gestures for optimal data capture and quality. Furthermore, the analytics and machine-learning feedback can also generate updated processes and practices for scanning device usage in the future. The training regimen can be used for team training and simulations, including new procedures simulations and high risk situation simulations, greatly assist in education and remedial situations addressing deficits and previous errors or omissions in scanning device usage, and can also identify and highlight human factor problems—fatigue, distraction, time limitation, and bias in an effort to provide more effective skin assessments.

In one example, the invention includes a training system to train an operator to use a hand-held monitor for early detection of a pathogenic bio-signal anomaly in a patient. The training system includes a housing sized to be hand-held by a user, a visual sensor in the housing, a thermal sensor in the housing, a location processor and memory to perform anatomical referencing to generate and store a motion path of the hand-held monitor relative to a portion of the patient's body based on data from the visual sensor and thermal sensor, and an application module to compare the stored motion path of the hand-held monitor to canonical motion path examples. Canonical motion path examples are recorded exemplary motion paths that indicate correct movement of the hand-held monitor.

In an embodiment of a server system application module 607, the application module provides computer-enabled Intelligent Skin Surveillance Alerts to drive action, clinical workflows & strengthen communication channels in the process of providing skin and injury interception and care. In this embodiment, the application defines custom escalations—enabling user-defined rules to be applied to triggers, timers, communication channels, tracking, and other analytics. In this embodiment, the application creates triggers to identify programmable categories, such as but not limited to high-risk or at-risk patients, or other categories such as pre-existing conditions, other clinical factors or the like. In one embodiment of programmable category, the alert system is triggered by SKEWS score, which prompts a bedside clinician to "intercept the injury", by providing preventative care prior to when the care would otherwise be provided without the system in place. The system prompts & documents appropriate intervention, including escalating the patient and their SKEWS score to the attention of the skin care team, and notifying caregivers to re-scan in a specific amount of time. In this embodiment, care providers can elect to "follow" or "unfollow" skin care patients in publication-subscription model not unlike "Twitter for Skin Care". The embodiment would further employ heuristic optimization—detecting skin condition outlier cases behind scenes, and providing long-term strategic care changes and corrections to the organization using the system.

In another embodiment of a server system application module, the application module performs intelligent Skin Surveillance combining thermal profile monitoring with visual future-casting of healing using machine learning and predictive analytics. The technique enables visual depiction of the optimal and sub-optimal trajectory for recovery from a skin incident and/or pathophysiological event, providing patient-centric visual and objective records of the skin's "journey" to healing, including "detours". The technique is based upon systematic, consistent, and comprehensive established and exploratory wound practice guidelines to create an incremental model of wound recovery stages. Machine learning algorithms are used to generate a predicted state of healing or pathophysiological condition resolution based on time since injury/condition onset, which is represented as both a visual and thermal image that conforms to the specific wound/pathophysiological condition geometry on the specific subject limb or body part. Deviation from either visual or thermal predictions can trigger alerts, prompting reassessment by a qualified professional, thus improving continuity of communication/documentation among varied providers and caregivers involved in the subject's care. During the care regimen, the subject is encouraged to perform injury and/or pathophysiological condition "selfies", which help reinforce the importance of adhering to care plan with patients and caregivers. Furthermore, the technique allows for Physician or caregiver profiling against their past and future predictions, which are incorporated into iterative changes in the machine learning model, therefore increasing accuracy of the predictions over time.

In another embodiment of a server system application module, the application module implements a skin and wound-care electronic reward-based system for providers, caregivers, and patients, to improve adherence to a plan of care or other quality/productivity metrics. In this embodiment, an outcome-based rewards model is used at various levels:

- At the scanning device user level, the device user is given rewards for achieving individual metrics for quality, compliance, or other metrics, including but not limited to the ratio of first-time images captured correctly. The system ranks device user peers and to industry and national norms; for example, awarding a "best scanner of the month" badge, tweeting or otherwise communicating leaderboard status, creating titles such as the "king scanner of floor 2".
- At the care-giver team level, where team incentives can help establish healthy competition between groups of caregivers
- At the subject level: where the system is designed to provide incentives for engagement in self-care activities (that contribute to quality outcomes), where awards could include but would not be limited to:
  - 45 days perfect "skin integrity"
  - Ability to earn badges, stars, status levels
  - Awards for completing educational "skin smart" modules
  - Rewards for progress with "skin safety goals"
  - Rewards for specific care outcomes, for example, "90 days w/o ulceration!"
  - Virtual or real currency awards, including loyalty program points (e.g. Walgreens Balance Rewards, CVS ExtraCare Points).

Figure 20:
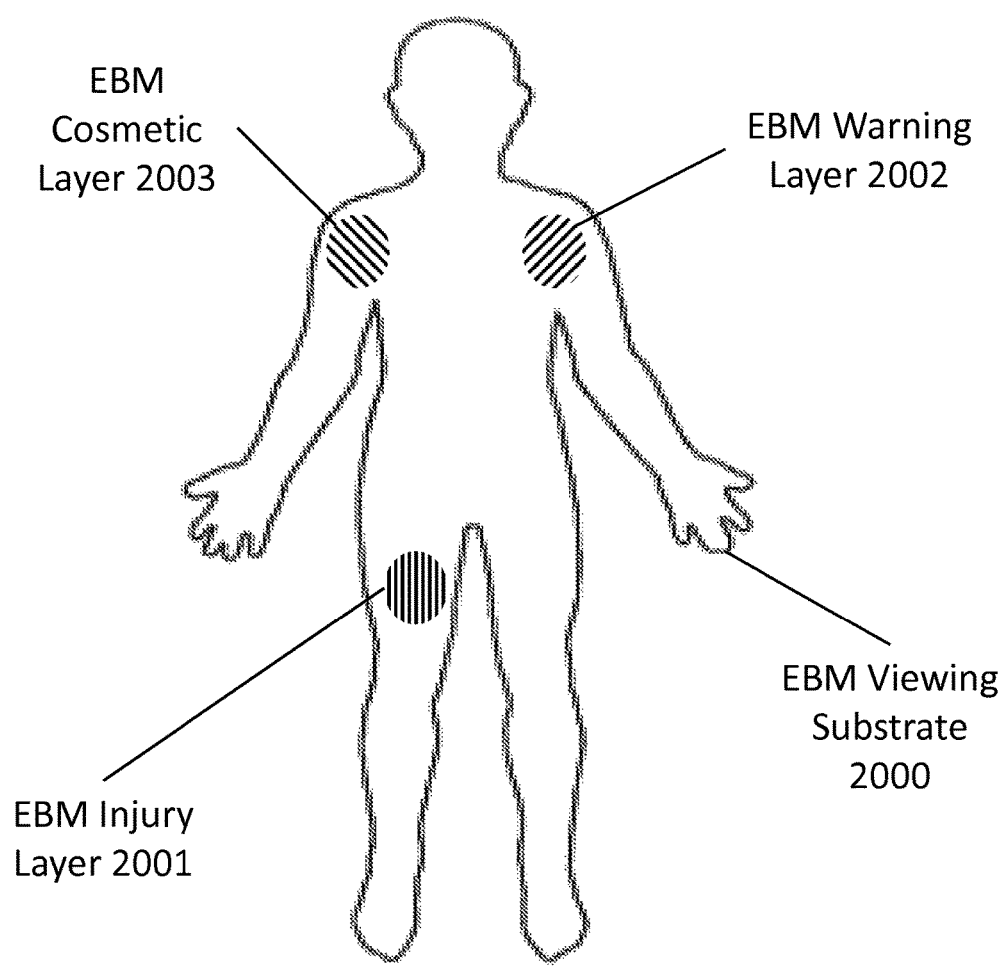
FIG. 20 shows another embodiment of a server system application module.

FIG. 20 shows another embodiment of a server system application module, where the application module builds, monitors and displays a series of stacked or un-stacked layers for an enhanced bio-signal map (EBM) of the state or status of soft tissue structures including, but not limited to skin, muscles, ligaments, tendons, wounds, joints, or blood vessels. The application shows, locates, and keeps history of the skin conditions on a EBM display substrate 2000 including but not limited to wounds, moles, allergy areas, skin imperfections, skin afflictions, complications of the skin, poor circulation, and scarring. In the preferred embodiment key factors (KF) are derived from non-contact or contact-based bio-signals such as but not limited to terahertz subdermal scanning, ultrasound, impedance, and spectroscopy bio-signals captured from the scanning device and processed within the server system, with combinations used to create the EBM. Processing and querying of the EBM can be accomplished via computer vision techniques, analytics and imaging techniques. The EBM, like a Google Earth map, will show many "areas of interest", pertaining to skin, including surrounding features, time-variant images and videos, and hyperlinks to related public information or information retrievable from the system itself. In one embodiment, the EBM could be displayed as a layer of information on a 3D body display such as the ZygoteBody from Zygote. In one embodiment, the EBM consists of three layers, the EBM Warning Layer 2002, which contains skin issues that are problematic and need further attention, the EBM Injury Layer 2001, which contains skin injuries (both past and current) and the EBM Cosmetic Layer 2003, which contains skin cosmetic issues. In the layered mode of this embodiment, each of the layers encapsulate a skin condition category and can be enabled or disabled for viewing, query, or other analysis.

Figure 19:
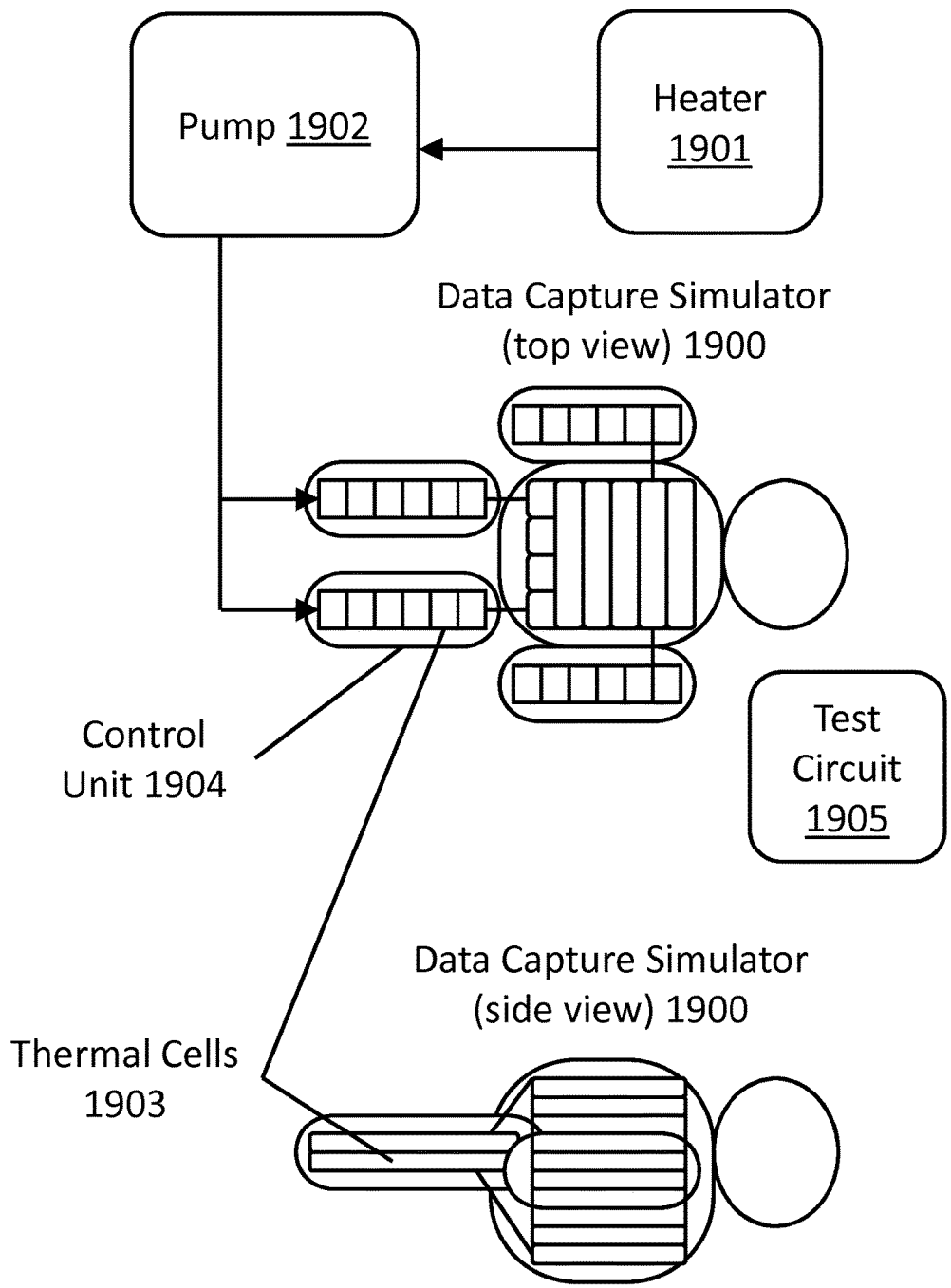
FIG. 19 shows an implementation of a thermal data capture simulator device that can be used to simulate thermal profiles on skin to aid in training and verification of skin scanning technique.

FIG. 19 shows an implementation of a thermal data capture simulator device 1900 that can be used to simulate thermal profiles on skin to aid in training and verification of skin scanning technique by the device user. In this embodiment, a heater 1901 is used to generate heat, which is injected into the simulator unit, which is formed in the shape of a human body, via a pump 1902. Thermal cells 1903, which consist of multiple circuits at different depths and are used to simulate vein depth and/or surrounding tissue, are actuated using a control unit 1904, allowing the simulator device to manifest thermal profiles at different locations, depths and thermal signatures on its surface. In one embodiment, interaction with the simulator device is verified via a test circuit 1905 that records touch or other input in the vicinity of the Thermal cell that was activated for a specific training episode.

In some embodiments, the systems and methods described herein are used for Eulerian video magnification of low frame rate super resolution infrared images adaptively combined with high frame rate visible light images for revealing subtle changes in the patient. The subtle changes can include breathing patterns while in low or no light situations. The low frame rate of infrared sensors is overcome by intelligently using the high frame rate visible light images to extrapolate, process, and adaptively provide the output revealing the subtle changes. Temporal processing allows a caregiver to know, for example, if the patient is breathing, and the rate at which the patient is breathing, while in darkened room. Feedback is in terms of vibrating the device or noise at the same pace of the respiration may be provided.

In other embodiments the systems and methods described herein are used for dynamic thermographic imaging combined with other arrayed bio-signals for monitoring muscle recruitment with range of motion ("ROM") and/or biomechanics measurements. SLAM may be used to assess and monitor range of motion at key joints and identify and compare muscle recruitment activity levels, for example via thermal profiles. The embodiments can provide unique biofeedback via real-time visual representations of activated muscle groups, blood-vessels, skin temperature and other bio-signals with motion underway. These embodiments can be sued for rehabilitation and sports training.

One of ordinary skill in the art will appreciate that the techniques, structures and methods of the present invention above are exemplary. The present inventions can be implemented in various embodiments without deviating from the scope of the invention.

The invention claimed is:

1. A scanner for detecting a latent pathogenic skin condition in a patient comprising:
    an infrared sensor configured to generate a first data set;
    an optical sensor configured to generate a second data set;
    an input module configured to receive one or more key factor input for the patient;
    a metrics module electrically connected to the infrared sensor, the optical sensor, and the input module, comprising a combinational and adaptive processor and memory, programmed to:

receive the one or more key factor input for the patient from the input module, acquire and store the first data set and the second data set, determine a combination weighted function based on the first and the second data sets, and compare the combination weighted function to a baseline of key indicators to determine that the latent pathogenic skin condition is present; and perform simultaneous localization and mapping of a portion of the patient's body with the infrared sensor and the optical sensor while the combinational and adaptive processor acquires the first data set and the second data set; and an accelerometer and a feature matching engine configured to receive simultaneously-captured visual images from the optical sensor and thermal images from the infrared sensor, perform feature detection on the visual images and thermal images, perform a homography calculation on the visual images and thermal images using timestamps from the accelerometer to align the detected features in the visual and thermal images, perform homography transformations on one or both of the visual images and thermal images, and perform image fusion on the resulting transformed image.

2. The scanner of claim 1 wherein the combinational and adaptive processor is programmed to generate temperature profiles for the portion of the patient's body from the first data set and the second data set while the combinational and adaptive processor acquires the first data set and the second data set.

3. The scanner of claim 1 wherein the combinational and adaptive processor is programmed to perform sizing and location analysis for the portion of the patient's body from the first data set and the second data set while the combinational and adaptive processor acquires the first data set and the second data set.

4. The scanner of claim 1 wherein the combinational and adaptive processor is programmed to perform the functions selected from the group consisting of skin matching, skin texture analysis, intelligent skin location identification, reflection analysis, color analysis, environmental temperature detection, and range determination from the first data set and the second data set while the combinational and adaptive processor acquires the first data set and the second data set.

5. The scanner of claim 1 further comprising: the feature matching engine is configured to use incremental alignment of successive visual images from the optical sensor to augment a thermal image from the infrared sensor to provide a super resolution thermal image adequate for anatomical referencing.

6. The scanner of claim 1 further comprising: a visible-light projector configured to project user interface elements onto the skin of the patient; and the infrared sensor is configured to detect user interactions with the projected user interface elements.

7. A monitoring system for detecting a latent pathogenic skin condition in a patient comprising:

an infrared sensor configured to generate a first data set and an optical sensor configured to generate a second data set;

an input module configured to receive one or more key factor input for the patient;

a metrics module electrically connected to the infrared sensor and the optical sensor and the input module, comprising a combinational and adaptive processor and memory, programmed to:

receive the one or more key factor input for the patient from the input module, acquire and store the first data set and the second data set, determine a combination weighted function based on the first and the second data sets, and compare the combination weighted function to a baseline of key indicators to determine that the latent pathogenic skin condition is present; and perform simultaneous localization and mapping of a portion of the patient's body with the infrared sensor and the optical sensor while the combinational and adaptive processor acquires the first data set and the second data set;

a feature matching engine configured to use an incremental alignment of successive visual images from the optical sensor to augment a thermal image from the infrared sensor to provide a super resolution thermal image adequate for anatomical referencing; and an accelerometer and the feature matching engine configured to receive simultaneously-captured visual images from the optical sensor and thermal images from the infrared sensor, perform feature detection on the visual images and thermal images, perform a homography calculation on the visual images and thermal images using timestamps from the accelerometer to align the detected features in the visual and thermal images, perform homography transformations on one or both of the visual images and thermal images, and perform image fusion on the resulting transformed image.

8. The system of claim 7 further comprising:

a visible-light projector configured to project user interface elements onto the skin of the patient; and the infrared sensor is configured to detect user interactions with the projected user interface elements.

9. The system of claim 7 further comprising: multiple real-time sensors selected from the group consisting of mono visible cameras, stereo visible cameras, mono infrared cameras, stereo infrared cameras, infrared pile sensors, spot measuring sensors, ambient temperature sensors, ambient light sensors, gas sensors, ultrasound sensors, near-infrared light sensors, gyroscopes, accelerometers, GPS sensors, Wi-Fi sensors, other location aware sensors, depth sensing sensors, bar ID scanners, patient ID scanners, terahertz sub-dermal scanners, ultrasound scanners, impedance spectroscopy sensors, and moisture sensors.

10. The system of claim 7 wherein the key indicator is selected from the group consisting of bio-signals, temperature profile, temperature differences, temperature comparisons, color indicators, color gradient indications, reflectivity indexes, texture indexes, area, areas interest, volume, contour heights, key performance markers, and key indicating factors.

11. The system of claim 7 wherein the one or more key factors are selected from the group consisting of data from the patient's Electronic Health Record ("EHR"), the patient's profile, key ratios for the combinational and adaptive processor, trigger points for the combinational and adaptive processor, priming functions for the combinational and adaptive processor, and override parameters.

12. The system of claim 7 wherein the baseline of key indicators is a population key indicator baseline.

13. The system of claim 7 wherein the baseline of key indicators is an individual key indicator baseline.

14. A method for detecting a latent pathogenic skin condition in a patient comprising:
   using an infrared sensor to generate a first data set;
   using an optical sensor to generate a second data set;
   using an input module to receive one or more key factor input for the patient;
   using a metrics module electrically connected to the infrared sensor, the optical sensor, and the input module, comprising a combinational and adaptive processor and memory, to
      receive with the metrics module the one or more key factor input for the patient from the input module,
      acquire and store with the metrics module the first data set and the second data set,
      determine with the metrics module a combination weighted function based on the first and the second data sets, and
      compare with the metrics module the combination weighted function to a baseline of key indicators to determine if that the latent pathogenic skin condition is present; and
      perform with the metrics module simultaneous localization and mapping of a portion of the patient's body with the infrared sensor and the optical sensor while the combinational and adaptive processor acquires the first data set and the second data set;
   projecting with a visible-light projector user interface elements onto the skin of the patient; and
   determining with the infrared sensor interactions with the projected user interface elements.

15. The method of claim 14 further comprising:
   using an accelerometer and a feature matching engine to receive simultaneously-captured visual images from the optical sensor and thermal images from the infrared sensor, perform feature detection on the visual images and thermal images, perform a homography calculation on the visual images and thermal images using timestamps from the accelerometer to align the detected features in the visual and thermal images, perform homography transformations on one or both of the visual images and thermal images, and perform image fusion on the resulting transformed image.

16. The method of claim 15 further comprising:
   using the feature matching engine to use an incremental alignment of successive visual images from the optical sensor to augment a thermal image from the infrared sensor to provide a super resolution thermal image adequate for anatomical referencing.

* * * * *